United States Patent
Reiser

(10) Patent No.: US 10,413,536 B2
(45) Date of Patent: *Sep. 17, 2019

(54) 6-ALKYNY-PYRIDINE DERIVATIVES

(71) Applicant: Boehringer Ingelheim International GmbH, Ingelheim am Rhein (DE)

(72) Inventor: Ulrich Reiser, Vienna (AT)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/715,351

(22) Filed: Sep. 26, 2017

(65) Prior Publication Data

US 2018/0015082 A1    Jan. 18, 2018

Related U.S. Application Data

(63) Continuation of application No. 15/283,494, filed on Oct. 3, 2016, now Pat. No. 9,801,871, which is a continuation of application No. 14/821,870, filed on Aug. 10, 2015, now Pat. No. 9,481,673.

(30) Foreign Application Priority Data

Aug. 11, 2014 (EP) .................................. 14180554

(51) Int. Cl.
*A61K 31/4709* (2006.01)
*C07D 471/04* (2006.01)
*A61K 31/506* (2006.01)

(52) U.S. Cl.
CPC ........ *A61K 31/4709* (2013.01); *A61K 31/506* (2013.01); *C07D 471/04* (2013.01)

(58) Field of Classification Search
None
See application file for complete search history.

(56) References Cited

U.S. PATENT DOCUMENTS

| | | |
|---|---|---|
| 8,859,541 B2 | 10/2014 | Reiser et al. |
| 9,249,151 B2 | 2/2016 | Reiser et al. |
| 9,278,978 B2 | 3/2016 | Reiser et al. |
| 9,481,673 B2* | 11/2016 | Reiser .................. C07D 471/04 |
| 9,801,871 B2* | 10/2017 | Reiser .................. C07D 471/04 |
| 2013/0225567 A1 | 8/2013 | Reiser et al. |
| 2015/0057286 A1 | 2/2015 | Reiser et al. |
| 2015/0057295 A1 | 2/2015 | Reiser et al. |

FOREIGN PATENT DOCUMENTS

| | | |
|---|---|---|
| WO | 2006113147 A2 | 10/2006 |
| WO | 2006133147 A2 | 12/2006 |
| WO | 2007101347 A1 | 9/2007 |
| WO | 2008073306 A1 | 6/2008 |
| WO | 2013127729 A1 | 9/2013 |
| WO | 2016023858 A1 | 2/2016 |

OTHER PUBLICATIONS

Bruno et al., "Targeting cytochrome P450 enzymes: A new approach in anti-cancer drug development", Science Direct, vol. 15, 2007, pp. 5047-5060.

International Search Report and written opinion for corresponding application PCT/EP2015/068349, dated Sep. 10, 2015.

(Continued)

*Primary Examiner* — Zinna Northington Davis
(74) *Attorney, Agent, or Firm* — Philip I. Datlow

(57) ABSTRACT

6-Alkynyl-pyridine of general formula (I)

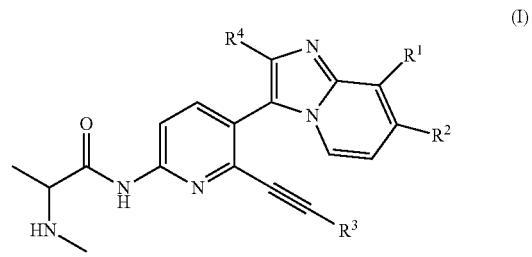

their use as SMAC mimetics, pharmaceutical compositions containing them, and their use as a medicaments for the treatment and/or prevention of diseases characterized by excessive or abnormal cell proliferation and associated conditions such as cancer.

An exemplary compound is

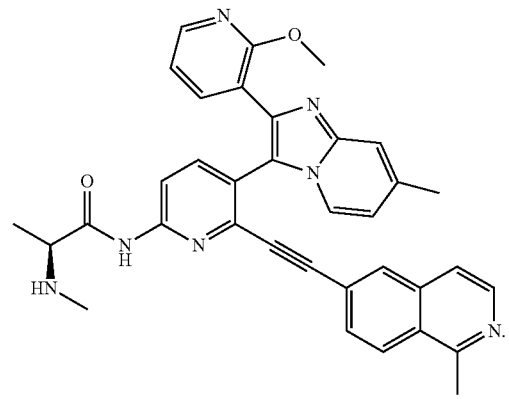

8 Claims, No Drawings

(56) References Cited

OTHER PUBLICATIONS

Choy, Pui Ying et al. "Palladium-Catalyzed Sonogashira Coupling of Aryl Mesylates and Tosylates" (2010) Chemistry A European Journal, vol. 16, 9982-9985.
Hansen, Marvin M. et al. "Boronic Acids and Derivatives—Probing the Structure—Activity Relationships for Mutagenicity" (2015) Org. Process Res. Dev., vol. 19, 1507-1516.
International Search Report PCT/EP2017/061885 dated Jul. 17, 2017.
International Search Report, Form PCT/ISA/210, and Written Opinion, Form PCT/ISA/237, for corresponding application PCT/EP2013/053689, dated Mar. 26, 2013.
Jordan et al., Binding of Carboxylic Acids by Fluorescent Pyridyl Ureas, J. Org Chem, 2010, 75, pp. 8450-8456.
Zhichkin, Paul E. et al. "The Use of Formamidine Protection for the Derivatization of Amiobenzoic Acids" (2008) Journal of Organic Chemistry, vol. 73, 8954-8959.

\* cited by examiner

6-ALKYNY-PYRIDINE DERIVATIVES

This invention relates to compounds of the general formula (I)

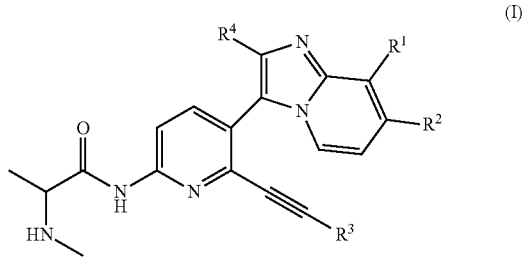

wherein the groups $R^1$ to $R^4$ have the meanings given in the claims and in the specification. The compounds of the invention are suitable for the treatment of diseases characterized by excessive or abnormal cell proliferation, pharmaceutical preparations containing such compounds and their uses as a medicament. The compounds of the invention modulate IAP activity.

BACKGROUND OF THE INVENTION

Apoptosis, a form of programmed cell death, typically occurs in the normal development and maintenance of healthy tissues in multicellular organisms. It is a complex process, which results in the removal of damaged, diseased or developmentally redundant cells, without signs of inflammation or necrosis. Apoptosis thus occurs as a normal part of development, the maintenance of normal cellular homeostasis, or as a consequence of stimuli such as chemotherapy and radiation.

The intrinsic apoptotic pathway is known to be deregulated in cancer and lymphoproliferative syndromes, as well as autoimmune disorders such as multiple sclerosis and rheumatoid arthritis. Additionally, alterations in a host apoptotic response have been described in the development or maintenance of viral and bacterial infections. Cancer cells gain the ability to overcome or circumvent apoptosis and continue with inappropriate proliferation despite strong pro-apoptotic signals such as hypoxia, endogenous cytokines, radiation treatments and chemotherapy. In autoimmune disease, pathogenic effector cells can become resistant to normal apoptotic cues. Resistance can be caused by numerous mechanisms, including alterations in the apoptotic machinery due to increased activity of anti-apoptotic pathways or expression of anti-apoptotic genes. Thus, approaches that reduce the threshold of apoptotic induction in cancer cells by overcoming resistance mechanisms may be of significant clinical utility.

Caspases serve as key effector molecules in apoptosis signaling. Caspases (cysteine containing aspartate specific proteases) are strong proteases and once activated, digest vital cell proteins from within the cell. Since caspases are highly active proteases, tight control of this family of proteins is necessary to prevent premature cell death. In general, caspases are synthesized as largely inactive zymogens that require proteolytic processing for activation. This proteolytic processing is only one of the ways in which caspases are regulated. The second mechanism of regulation is through a family of proteins that bind and inhibit caspases.

One family of molecules that inhibit caspases are the Inhibitors of Apoptosis (IAP) (Deveraux et al., J Clin Immunol (1999), 19: 388-398). IAPs were originally discovered in baculovirus by their ability to substitute for P35 protein function, an anti-apoptotic gene (Crook et al. (1993) J Virology 67, 2168-2174). Human IAPs are characterized by the presence of one to three homologous structural domains known as baculovirus IAP repeat (BIR) domains. Some IAP family members also contain a RING zinc finger domain at the C-terminus, with the capability to ubiquitylate target proteins via their E3 ligase function. The human IAPs, XIAP, HIAP1 (also referred to as cIAP2), and HIAP2 (cIAP1) each have three BIR domains, and a carboxy terminal RING zinc finger. Another IAP, NAIP, has three BIR domains (BIR1, BIR2 and BIR3), but no RING domain, whereas Livin, TsIAP and MLIAP have a single BIR domain and a RING domain. The X chromosome-linked inhibitor of apoptosis (XIAP) is an example of an IAP, which can inhibit the initiator caspase Caspase-9, and the effector caspases, Caspase-3 and Caspase-7, by direct binding. XIAP can also induce the degradation of caspases through the ubiquitylation-mediated proteasome pathway via the E3 ligase activity of a RING zinc finger domain. Inhibition of Caspase-9 is mediated by the BIR3 domains of XIAP, whereas effector caspases are inhibited by binding to the linker-BIR2 domain. The BIR domains also mediate the interactions of IAPs with tumor necrosis factor-receptor associated factor (TRAFs)-I and -2, and with TAB1, adaptor proteins affecting survival signaling through NFkB activation. IAP proteins can thus function as direct brakes on the apoptosis cascade by inhibiting active caspases or by redirecting cellular signaling to a pro-survival mode. Survivin is another member of the IAP family of antiapoptotic proteins. It is shown to be conserved in function across evolution as homologues of the protein are found both in vertebrates and invertebrates.

Cancer cells and cells involved in autoimmune disease may avoid apoptosis by the sustained over-expression of one or more members of the IAP family of proteins. For example, IAP overexpression has been demonstrated to be prognostic of poor clinical outcome in multiple cancers, and decreased IAP expression through RNAi strategies sensitizes tumor cells to a wide variety of apoptotic insults including chemotherapy, radiotherapy and death receptor ligands. For XIAP, this is shown in cancers as diverse as leukemia and ovarian cancer. Over expression of cIAP1 and cIAP2 resulting from the frequent chromosome amplification of the 11q21-q23 region, which encompasses both genes, has been observed in a variety of malignancies, including medulloblastomas, renal cell carcinomas, glioblastomas, and gastric carcinomas.

The interaction between the baculoviral IAP repeat-3 (BIR3) domain of X-linked inhibitor of apoptosis (XIAP) and caspase-9 is of therapeutic interest because this interaction is inhibited by the NH2-terminal seven-amino-acid residues of the so-called "second mitochondrial-derived activator of caspase" (in short and hereinafter SMAC), a naturally occurring antagonist of IAPs. Small-molecule SMAC mimetics have been generated anticipating efficacy in cancer by reconstituting apoptotic signaling.

Thus, there is the need to provide SMAC mimetics useful for the prevention and/or treatment of diseases characterized by excessive or abnormal cell proliferation, such as cancer.

The aim of the present invention is to provide new compounds which can be used for the prevention and/or treatment of diseases characterized by excessive or abnormal cell proliferation, in particular in the treatment of cancer. The compounds according to the invention are characterized by a powerful inhibitory effect of IAP-SMAC protein-protein-interaction.

In addition to powerful inhibition of the IAP-SMAC protein-protein-interaction, for the development of pharmaceutical products it is important that the active agent shows low inhibition of P450 as recommended in the Guidelines of the FDA. It is desirable to have compounds which show low inhibition of P450 isoenzymes ideally with IC50 values greater than 5 µM.

6-alkynyl-pyridine derivatives as SMAC mimetics or IAP inhibitors are also described in WO 2013/127729.

Table 1 summarizes some examples of the prior art document WO 2013/127729 which are characterized by a 6-membered heteroaryl substituent attached to the imidazo[1,2-a]pyridine in position 5 of the central pyridine ring together with their IC50 values representing the inhibition of the five P450 isoenzymes and their solubility values.

For the compounds of Table 1, it has been found that for 3-5 of five P450 isoenzymes the IC50 is lower than 5 µM.

As mentioned above the desirable range of the inhibition of the P450 isoenzyme is an IC50 greater 5 µM. More preferably, for all of the five isoenzymes the IC50 is greater than 5 µM.

Accordingly, there is the need to provide compounds characterized by a 6-membered heteroaryl substituent on an imidazo[1,2-a]pyridine in position 5 of the central pyridine ring which show lower inhibition of the P450 isoenzymes, represented by IC50 values greater than 5 µM.

The compounds of the invention differ from the compounds of Table 1 in that the 5-6 membered heteroaryl is further substituted with an alkyl group or a oxyalkyl group.

Surprisingly, the compounds of the invention show lower P450 inhibition meaning that no or at maximum 2 of 5 P450 isoenzymes show inhibitory values with IC50<5 µM.

Accordingly, the compounds of the invention show a powerful inhibitory effect of IAP-SMAC protein-protein-interaction and low inhibition of the P450 isoenzymes.

Preferred compounds of the invention are those which combine powerful inhibition of IAP-SMAC protein-protein interaction, low inhibition of the P450 isoenzymes and solubility greater than 10 µg/ml at pH 6.8.

TABLE 1

Measured examples from WO 2013/127729 inhibit many P450 isoenzymes already at concentrations below 5 µM and predominately show low solubility at pH 6.8.

| Ex # | Structure | P450 2C19 | P450 2C8 | P450 2C9 | P450 2D6 | P450 3A4 | Solubility pH 6.8 [µg/ml] |
|---|---|---|---|---|---|---|---|
| 27 | 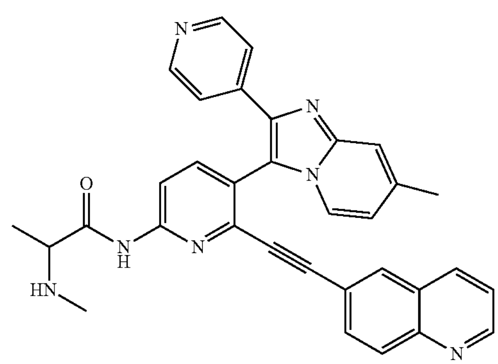 [SMILES: CNC(C)C(=O)Nc1ccc(-c2c(-c3ccncc3)nc3cc(C)ccn23)c(C#Cc2ccc3ncccc3c2)n1] | 5.3 | 0.3 | 0.4 | 9.3 | 3.7 | 3 |
| 64 | 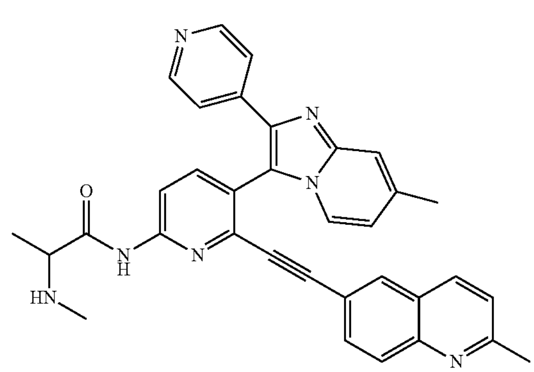 [SMILES: CNC(C)C(=O)Nc1ccc(-c2c(-c3ccncc3)nc3cc(C)ccn23)c(C#Cc2ccc3nc(C)ccc3c2)n1] | 4.3 | 0.5 | 0.4 | 5.2 | 2.1 | N/A |

TABLE 1-continued

Measured examples from WO 2013/127729 inhibit many P450 isoenzymes already at concentrations below 5 μM and predominately show low solubility at pH 6.8.

| Ex # | Structure | P450 2C19 | P450 2C8 | P450 2C9 | P450 2D6 | P450 3A4 | Solubility pH 6.8 [μg/ml] |
|---|---|---|---|---|---|---|---|
| 81 | 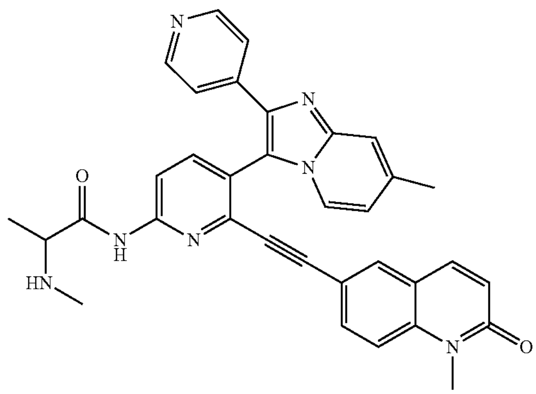 | 2.8 | 1.2 | 0.9 | 3.4 | 4.0 | 8 |
| 82 | 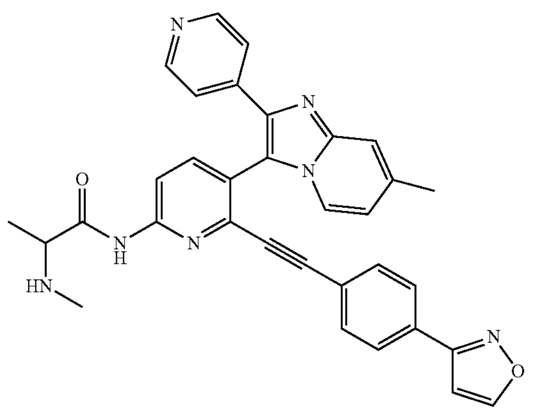 [SMILES: CNC(C)C(=O)Nc1ccc(-c2c(-c3ccncc3)nc3cc(C)ccn23)c(C#Cc2ccc(-c3ccon3)cc2)n1] | 4.8 | 0.3 | 0.4 | 2.2 | 2.3 | N/A |
| 94 | 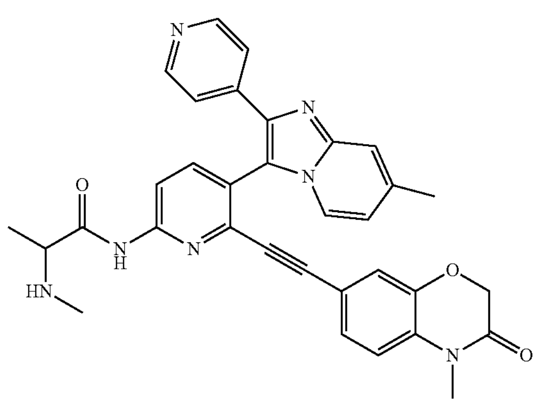 [SMILES: CNC(C)C(=O)Nc1ccc(-c2c(-c3ccncc3)nc3cc(C)ccn23)c(C#Cc2ccc3c(c2)OCC(=O)N3C)n1] | 2.9 | 4.9 | 0.7 | 3.3 | >50 | N/A |

TABLE 1-continued

Measured examples from WO 2013/127729 inhibit many P450 isoenzymes already at concentrations below 5 µM and predominately show low solubility at pH 6.8.

| Ex # | Structure | P450 2C19 | P450 2C8 | P450 2C9 | P450 2D6 | P450 3A4 | Solubility pH 6.8 [µg/ml] |
|---|---|---|---|---|---|---|---|
| 185 | 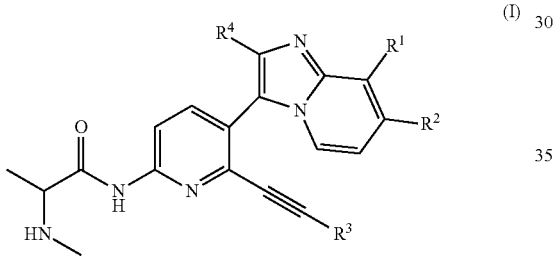 | 16 | 1.7 | 4.8 | 2.7 | 3.0 | 60 |

DETAILED DESCRIPTION OF THE INVENTION

The present invention relates to compounds of formula (I)

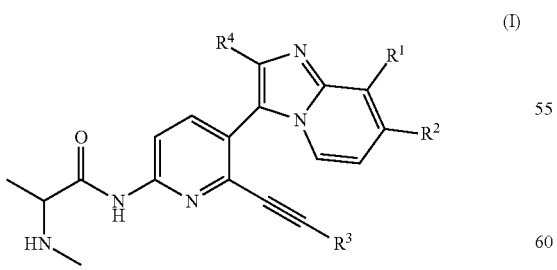

(I)

wherein $R^1$ to $R^4$ are as defined in the description and in the claims. The compounds according to formula (I) act as SMAC mimetics. Thus, the compounds of the invention may be used for example for the treatment of diseases which are characterized by an increased apoptosis threshold due to overexpression of IAP protein. Preferably, the compounds of the invention can be used in the treatment of cancer.

The present invention therefore relates to compounds of general formula (I)

(I)

Wherein
$R^1$ is selected from the group consisting of hydrogen, —$C_{1-3}$alkyl and halogen;
$R^2$ is selected from the group consisting of hydrogen, —$C_{1-3}$alkyl and halogen;
$R^3$ is selected from phenyl or a 9- to 14-membered heteroaryl wherein each of these groups is optionally substituted with $R^5$ or
$R^3$ is a phenyl moiety fused with a 5-6 membered heterocycloalkyl, wherein each of these groups is optionally and independently substituted with one or more $R^6$;
$R^4$ is a 5- or 6-membered heteroaryl substituted with —$C_{1-3}$alkyl or —O—$C_{1-3}$alkyl;
$R^5$ is —$C_{1-3}$alkyl;
$R^6$ is =O or —$C_{1-3}$alkyl;
and wherein the compounds of formula (I) may optionally be present in the form of salts.

In a preferred embodiment the invention relates to compounds of formula (I), wherein $R^1$ is selected from hydrogen, —$CH_3$, —Cl.

In a preferred embodiment the invention relates to compounds of formula (I), wherein $R^2$ is selected from —H, —$CH_3$, —Cl.

In a preferred embodiment the invention relates to compounds of formula (I), wherein $R^1$ is hydrogen and $R^2$ is selected from hydrogen, —$CH_3$ and Cl.

In a preferred embodiment the invention relates to compounds of formula (I), wherein $R^4$ is a 6-membered heteroaryl substituted with —$C_{1-3}$alkyl or —O—$C_{1-3}$alkyl.

In a preferred embodiment the invention relates to compounds of formula (I), wherein $R^4$ is a 6-membered heteroaryl substituted with —$CH_3$ or —O—$CH_3$.

In a preferred embodiment the invention relates to compounds of formula (I), wherein $R^4$ is selected from pyridyl, pyrimidinyl, pyrazolyl, imidazolyl, each of which is independently substituted with —$C_{1-3}$alkyl or —O—$C_{1-3}$alkyl.

In a preferred embodiment the invention relates to compounds of formula (I), wherein $R^4$ is selected from pyridyl, pyrimidinyl, pyrazolyl, imidazolyl, each of which is independently substituted with —$CH_3$ or —O—$CH_3$.

In a preferred embodiment the invention relates to compounds of formula (I), wherein $R^4$ is pyridyl substituted with —$CH_3$.

In a preferred embodiment the invention relates to compounds of formula (I), wherein $R^4$ is pyridyl substituted with —O—$CH_3$.

In a preferred embodiment the invention relates to compounds of formula (I), wherein $R^4$ is pyrimidinyl substituted with —$CH_3$.

In a preferred embodiment the invention relates to compounds of formula (I), wherein $R^4$ is pyrazolyl substituted with —$CH_3$.

In a preferred embodiment the invention relates to compounds of formula (I), wherein $R^4$ is imidazolyl substituted with —$CH_3$.

In a preferred embodiment the invention relates to compounds of formula (I), wherein $R^3$ is selected phenyl,

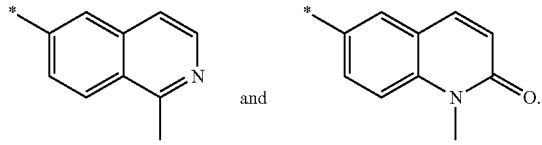 [SMILES: *c1ccc2c(C)nccc2c1 ; *c1ccc2c(ccc(=O)n2C)c1]

and

In a preferred embodiment the invention relates to compounds of formula (I), wherein $R^3$ is

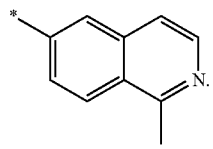

In a preferred embodiment the invention relates to compounds of formula (I), wherein $R^3$ is

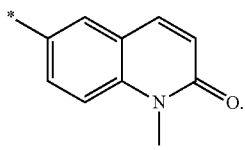

In another aspect the invention relates to compounds of general formula (I) or of anyone of the embodiments as disclosed above for use in the treatment of cancer.

In another aspect the invention relates to compounds of general formula (I) or of anyone of the embodiments as disclosed above—or the pharmaceutically acceptable salts thereof—for use as medicaments.

In another aspect the invention relates to compounds of general formula (I) or of anyone of the embodiments as disclosed above—or the pharmaceutically acceptable salts thereof—for use in the treatment and/or prevention of cancer, infections, inflammations and autoimmune diseases.

In another aspect the invention relates to compounds of general formula (I) or of anyone of the embodiments as disclosed above—or the pharmaceutically acceptable salts thereof—for use in the treatment and/or prevention of cancer, preferably of carcinomas of the breast, in particular triple negative breast cancer (TNBC), prostate, brain or ovary, non-small-cell lung carcinomas (NSCLC), melanomas, acute myeloid leukaemia (AML) and chronic lymphatic leukaemias (CLL).

In another aspect the invention relates to compounds of general formula (I) or of anyone of the embodiments as disclosed above—or the pharmaceutically acceptable salts thereof—for use in the treatment and/or prevention of carcinomas of the breast, in particular triple negative breast cancer (TNBC), prostate, brain or ovary, non-small-cell lung carcinomas (NSCLC), melanomas, acute myeloid leukaemia (AML) and chronic lymphatic leukaemias (CLL).

In another aspect the invention relates to a method for the treatment and/or prevention of cancer comprising administering a therapeutically effective amount of a compound of general formula (I) or of anyone of the embodiments as disclosed above—or one of the pharmaceutically acceptable salts thereof—to a human being.

In another aspect the invention relates to a method for the treatment and/or prevention of carcinoma of the breast, in particular triple negative breast cancer (TNBC), prostate, brain or ovary, non-small-cell lung carcinomas (NSCLC), melanomas acute myeloid leukaemia (AML) and chronic lymphatic leukemias (CLL) comprising administering a therapeutically effective amount of a compound of general formula (I) or of anyone of the embodiments as disclosed above—or one of the pharmaceutically acceptable salts thereof—to a human being.

In another aspect the invention relates to a pharmaceutical preparation containing as active substance one or more compounds of general formula (I) or of anyone of the embodiments as disclosed above—or the pharmaceutically acceptable salts thereof—optionally in combination with conventional excipients and/or carriers.

In another aspect the invention relates to a pharmaceutical preparation comprising a compound of general formula (I) or of anyone of the embodiments as disclosed above—or one of the pharmaceutically acceptable salts thereof—and at least one other cytostatic or cytotoxic active substance, different from formula (I).

Definitions

Terms that are not specifically defined here have the meanings that are apparent to the skilled man in the light of the overall disclosure and the context as a whole.

As used herein, the following definitions apply, unless stated otherwise:

In the groups, radicals, or moieties defined below, the number of carbon atoms is often specified preceding the group, for example, —$C_{1-5}$alkyl means an alkyl group or radical having 1 to 5 carbon atoms. In general, for groups comprising two or more subgroups, the first named subgroup is the radical attachment point, for example the substitutent —$C_{1-5}$alkyl-$C_{3-10}$cylcoalkyl, means a $C_{3-10}$cylcoalkyl group which is bound to a $C_{1-5}$alkyl, the latter of which is bound to the core structure or to the group to which the substitutent is attached.

The indication of the number of members in groups that contain one or more heteroatom(s) (heteroalkyl, heteroaryl, heteroarylalkyl, heterocyclyl, heterocycylalkyl) relates to the total atomic number of all the ring members or chain members or the total of all the ring and chain members.

The person skilled in the art will appreciate that substituent groups containing a nitrogen atom can also be indicated as amine or amino. Similarly, groups containing oxygen atom can also be indicated with -oxy, like for example alkoxy. Groups containing —C(O)— can also be indicated as carboxy; groups containing —NC(O)— can also be indicated as amide; groups containing —NC(O)N— can also be indicated as urea; groups containing —NS(O)$_2$— can also be indicated as sulfonamide.

Alkyl denotes monovalent, saturated hydrocarbon chains, which may be present in both linear and branched form. If an alkyl is substituted, the substitution may take place independently of one another, by mono- or polysubstitution in each case, on all the hydrogen-carrying carbon atoms.

The term "$C_{1-5}$-alkyl" includes for example methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$).

By the terms propyl, butyl, pentyl, etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy or $C_{x-y}$-alkoxy, wherein $C_{x-y}$-alkyloxy and $C_{x-y}$-alkoxy indicate the same group.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$, —$CH_2CH_3$ and —$CH_2CH_2$ or >$CHCH_3$ etc.

The term "$C_{1-4}$-alkylene" includes for example —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CHCH(CH_3)_2)$— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another group such as for example in HO—$C_{x-y}$-alkylenamino or $H_2N$—$C_{x-y}$-alkylenoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenylenamino or $H_2N$—$C_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl.

By the generic terms propynyl, butynyl, pentynyl, etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl.

If a hydrocarbon chain carries both at least one double bond and also at least one triple bond, by definition it belongs to the alkynyl subgroup.

The above definition for alkynyl also applies if alkynyl is part of another group, as in $C_{x-y}$-alkynylamino or $C_{x-y}$-alkynyloxy, for example.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, ect. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x-y}$-alkynyleneamino or $H_2N$—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —Cl=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —$CH_2F$ and —CHF—, —$CHFCH_2F$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0] decyl (decahydronaphthalene), bicyclo[2.2.1]heptyl (norbornyl), bicyclo[4.1.0]heptyl (norcaranyl), bicyclo[3.1.1] heptyl (pinanyl), spiro[2.5]loctyl, spiro[3.3]heptyl etc.

The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained.

The term cycloalkylene can thus be derived from the previously defined cycloalkyl.

Cycloalkylene, unlike cycloalkyl, is bivalent and requires two binding partners. Formally, the second valency is obtained by removing a hydrogen atom from a cycloalkyl. Corresponding groups are for example cyclohexyl and

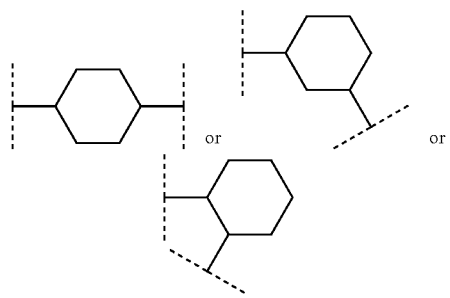

(cyclohexylene). The above definition for cycloalkylene also applies if cycloalkylene is part of another group as in HO—$C_{x-y}$-cycloalkyleneamino or $H_2N$—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4.5]dec-2-ene etc.

The above definition for cycloalkenyl also applies when cycloalkenyl is part of another group as in $C_{x-y}$-cycloalkenylamino or $C_{x-y}$-cycloalkenyloxy, for example.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example cyclopentenyl and

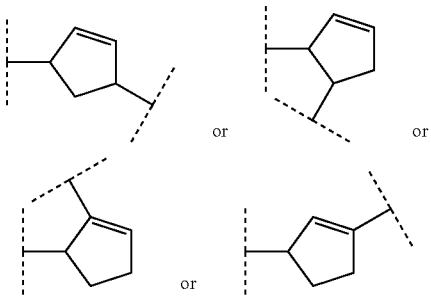

(cyclopentenylene) etc.

The above definition for cycloalkenylene also applies when cycloalkenylene is part of another group as in HO—$C_{x-y}$-cycloalkenyleneamino or $H_2N$—$C_{x-y}$-cycloalkenyleneoxy, for example.

Aryl denotes a mono-, bi- or tricyclic group with at least one aromatic carbocycle. Preferably it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g. phenyl and

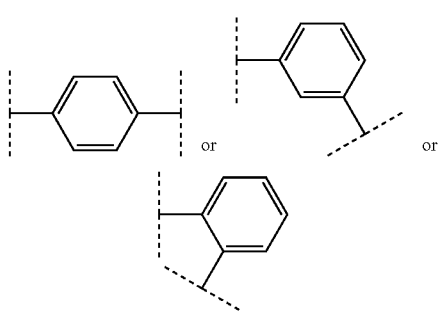

(o, m, p-phenylene), naphthyl and

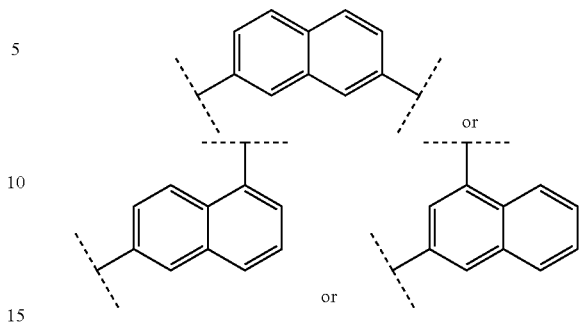

etc.

The above definition for arylene also applies when arylene is part of another group as in HO-aryleneamino or $H_2N$-aryleneoxy for example.

Heterocyclyl denotes ring systems, which are derived from the previously defined cycloalkyl, cycloalkenyl and aryl by replacing one or more of the groups —$CH_2$-independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO, sulphone —$SO_2$—; nitroge→N-oxide).

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. Saturated and unsaturated, non-aromatic, heterocyclyl are also defined as heterocycloalkyl. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. When the heterocyclyl has a nitrogen atom, the preferred position to bind the heterocyclyl substituent to the molecule is the nitrogen atom.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1.4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-azabicyclo[3.2.1]octyl, 8-azabicyclo[5.1.0]octyl, 2-oxa-5-azabicyclo[2.2.1]heptyl, 8-oxa-3-aza-bicyclo

[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]-nonyl, 1,4-dioxa-spiro[4.5]decyl, 1-oxa-3,8-diaza-spiro[4.5]decyl, 2,6-diaza-spiro[3.3]-heptyl, 2,7-diaza-spiro[4.4]nonyl, 2,6-diaza-spiro[3.4]octyl, 3,9-diaza-spiro[5.5]undecyl, 2,8-diaza-spiro[4.5]decyl etc.

Further examples are the structures illustrated below, which may be attached via each hydrogen-carrying atom (exchanged for hydrogen):

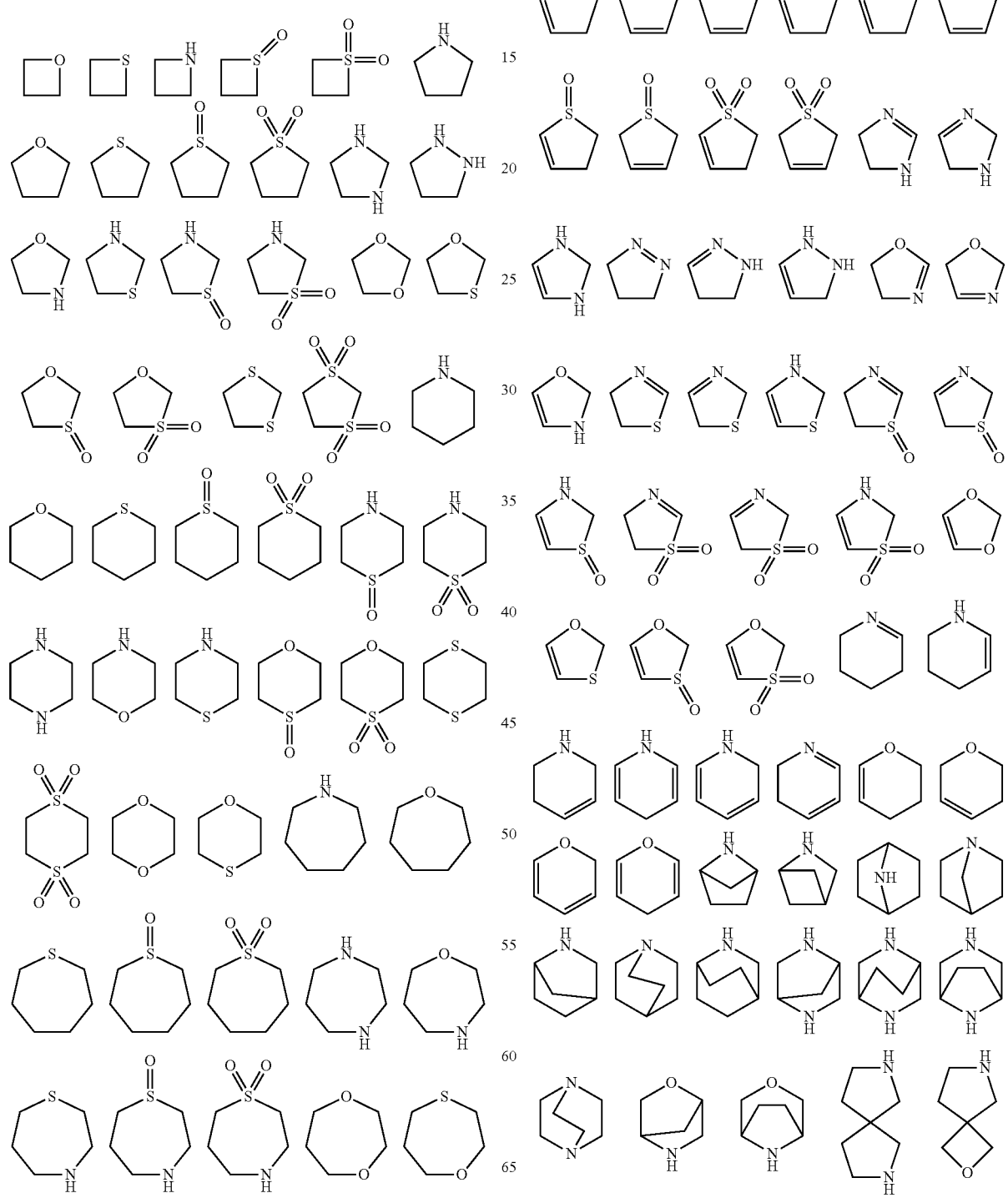

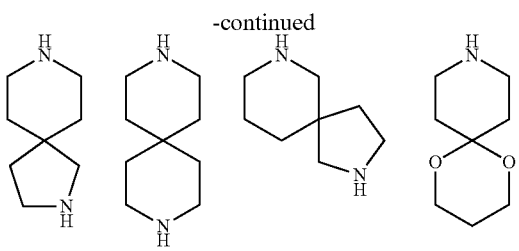

The above definition of heterocyclyl also applies if heterocyclyl is part of another group as in heterocyclylamino or heterocyclyloxy for example.

If the free valency of a heteroyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example piperidinyl and

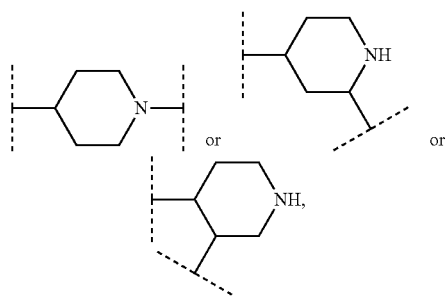

2,3-dihydro-1H-pyrrolyl and

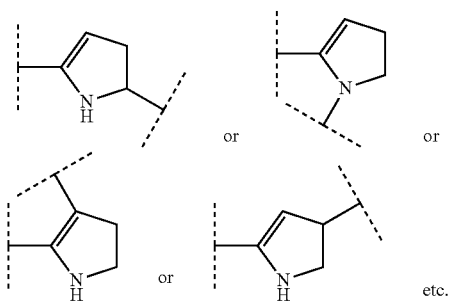

The above definition of heterocyclylene also applies if heterocyclylene is part of another group as in HO-heterocyclyleneamino or H$_2$N-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

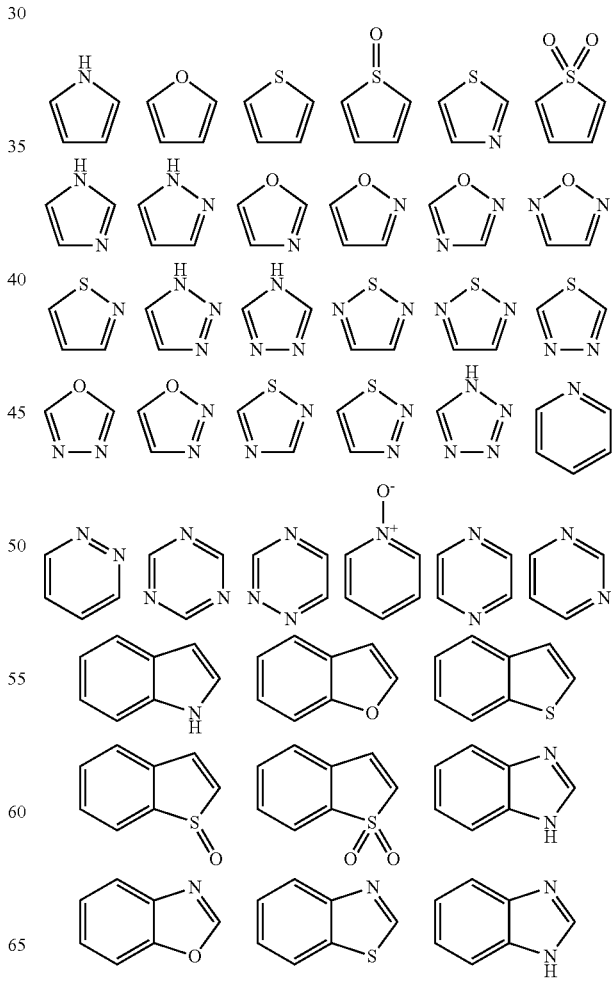

-continued

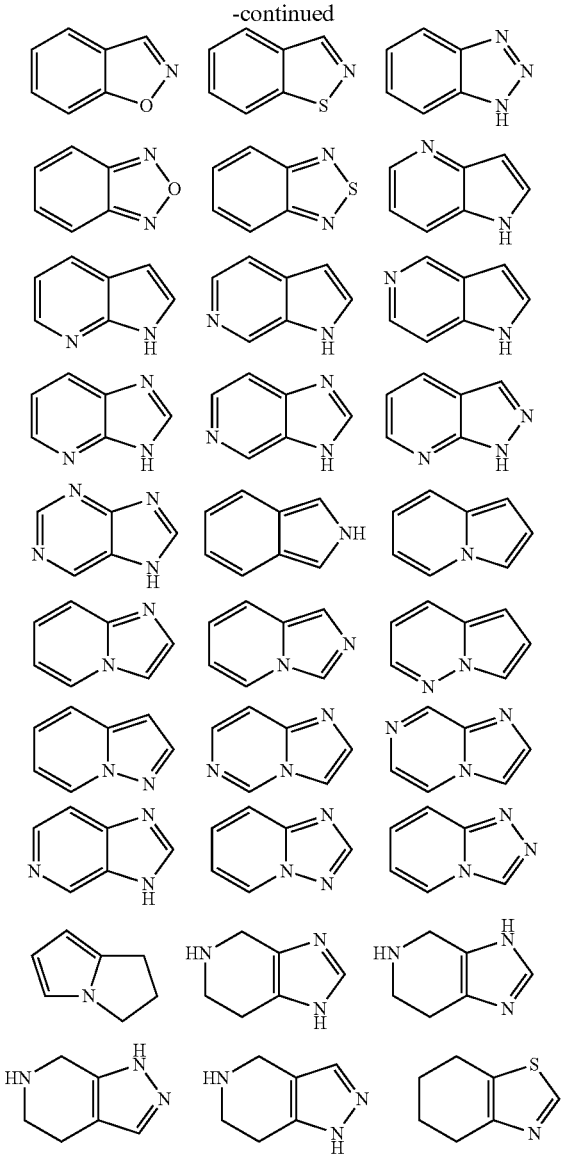

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl. Corresponding groups are for example pyrrolyl and

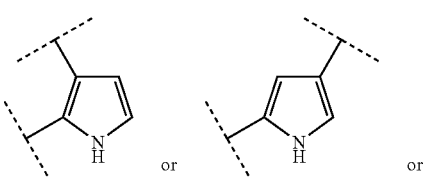

-continued

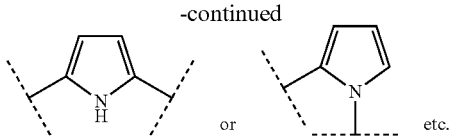

The above definition of heteroarylene also applies when heteroarylene is part of another group as in HO-heteroaryleneamino or $H_2N$-heteroaryleneoxy, for example.

The bivalent groups mentioned above (alkylene, alkenylene, alkynylene etc.) may also be part of composite groups (e.g. $H_2N$—$C_{1-4}$alkylene- or HO—$C_{1-4}$alkylene-). In this case one of the valencies is saturated by the attached group (here: —$NH_2$, —OH), so that a composite group of this kind written in this way is only a monovalent substituent over all.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =$N_2$ or the like, may only be substituted at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —$CH_2$— or sulphur atoms of a ring system.

Stereochemistry/Solvates/Hydrates: Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally, for the purposes of the present invention the solvated forms, e.g. hydrates, are to be regarded as of equal value to the unsolvated forms.

Salts: The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio.

The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsnilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound, which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof).

Salts of acids other than those mentioned above, which are useful for example for purifying or isolating the compounds from the reaction mixtures (e.g. trifluoroacetates), are also to be regarded as part of the invention.

In a representation such as for example

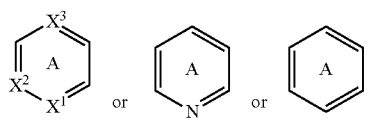

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

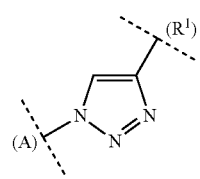

or $(R^2)$—C(O)NH— or $(R^2)$—NHC(O)—;

Groups or substituents are frequently selected from among a number of alternative groups/substituents with a corresponding group designation (e.g. $R^a$, $R^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

| List of abbreviations | |
|---|---|
| ACN | acetonitrile |
| Bu | butyl |
| conc. | concentrated |
| d | day(s) |
| DCM | dichloromethane |
| Et | ethyl |
| EtOAc | Ethyl acetate |
| h | hour(s) |
| HPLC | high performance liquid chromatography |
| iPr | isopropyl |
| M | molar |
| Me | methyl |
| min | minute(s) |
| mL | millilitre |
| MS | mass spectrometry |
| N | normal |
| NMP | N-methylpyrrolindinone |
| NMR | nuclear resonance spectroscopy |
| NP | normal phase |
| ppm | part per million |
| prep | preparative |
| $R_f$ | retention factor |
| RP | reversed phase |
| RT | room temperature |
| tert | tertiary |
| TFA | trifluoroacetic acid |
| THF | tetrahydrofuran |
| TLC | thin layer chromatography |
| tR | retention time |

Other features and advantages of the present invention will become apparent from the following more detailed examples which exemplarily illustrate the principles of the invention without restricting its scope.

General

Unless stated otherwise, all the reactions are carried out in commercially obtainable apparatuses using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with IUPAC guidelines. If a compound is to be represented both by a structural formula and by its nomenclature, in the event of a conflict the structural formula is decisive.

Chromatography

Thin layer chromatography is carried out on ready-made TLC plates of silica gel 60 on glass (with fluorescence indicator F-254) made by Merck.

A Biotage Isolera Four apparatus is used for automated preparative NP chromatography together with Interchim Puri Flash columns (50 μm, 12-300 g) or glass columns filled with silica gel made by Millipore (Granula Silica Si-60A 35-70 μm).

Preparative RP HPLC is carried out with columns made by Waters (Sunfire C18, 10 μm, 30×100 mm Part. No.

186003971 or X-Bridge C18, 10 μm, 30×100 mm Part. No. 186003930). The compounds are eluted using either different gradients of H₂O/acetonitrile or H₂O/MeOH, where 0.2% HCOOH is added to the water, or with different gradients utilizing a basic aqueous buffer solution (1 L water contains 5 mL of an ammonium hydrogencarbonate solution (158 g per 1 L H₂O) and 2 mL ammonia (7 mol/l solution in MeOH)) instead of the water-HCOOH-mixture.

The analytical HPLC (reaction monitoring) of intermediate compounds is carried out with columns made by Agilent and Waters. The analytical equipment is also provided with a mass detector in each case.

HPLC Mass Spectroscopy/UV Spectrometry

The retention times/MS-ESI⁺ for characterising the example compounds according to the invention are determined using an HPLC-MS apparatus (high performance liquid chromatography with mass detector) made by Agilent. Compounds that elute at the injection peak are given the retention time tR=0.

Analytical HPLC Methods (A.M.)
Method_1 (M_1)
HPLC: Agilent 1100 Series
MS: Agilent LC/MSD SL
Column: Waters, Xbridge C18, 2.5 μm, 2.1×20 mm, Part. No. 186003201
Solvent: A: 20 mM NH₄HCO₃/NH₃
B: ACN HPLC grade
Detection: MS: Positive and negative
Mass range: 120-800 m/z
Injection: 5 μL
Flow: 1.00 mL/min
Column temp.: 60° C.
Gradient: 0.00-1.50 min 10%→95% B
1.50-2.00 min 95% B
2.00-2.10 min 95%→10% B
Method_2 (M_2)
HPLC: Agilent 1100/1200 Series
MS: Agilent LC/MSD SL
Column: Waters X-Bridge BEH C18, 2.5 μm, 2.1×30 mm
Eluant: A: 5 mM NH₄HCO₃/19 mM NH₃ in H₂O; B: ACN (HPLC grade)
Detection: MS: Positive and negative mode ESI
Mass range: 100-800 m/z
Flow: 1.4 ml/min
Column temp.: 45° C.
Gradient: 0.00-0.01 min→5% B
0.01-1.00 min: 5%→100% B
1.00-1.37 min: 100% B
1.37-1.40 min: 100%→5% B
Method_3 (M_3)
HPLC: Agilent 1100 Series
MS: Agilent LC/MSD SL
Column: WatersXBridge C18, 5.0 μm, 2.1×50 mm
Eluant: A: 5 mM NH₄HCO₃/19 mM NH₃ in H₂O; B: ACN (HPLC grade)
Detection: MS: Positive and negative mode ESI
Mass range: 105-1200 m/z
Flow: 1.20 ml/min
Column temp.: 35° C.
Gradient: 0.00-0.01 min: 5% B
0.01-1.25 min: 5%→95% B
1.25-2.00 min: 95% B
2.00-2.01 min: 95%→5% B
Method_4 (M_4)
HPLC: Agilent 1100/1200 Series
MS: Agilent LC/MSD SL
Column: Waters Sunfire, C18, 5.0 μm, 2.1×50 mm, Part. No. 186002539
Eluant: A: H₂O+0.2% HCOOH; B: ACN
Detection: MS: Positive and negative mode ESI
Mass range: 105-1200 m/z
Flow: 1.20 ml/min
Column temp.: 35° C.
Gradient: 0.00-0.01 min: 5% B
0.01-1.50 min: 5%→95% B
1.50-2.00 min: 100% B Preparation of the Compounds According to the Invention The compounds according to the invention are prepared by methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in literature are prepared according to the published methods.

One method for the preparation of compounds of formula (I) is exemplified in Scheme I: 5,6-dibromopyridin-2-amine A is coupled with a trialkylsilylacetylene to obtain an intermediate B which is converted into intermediate C via amidation. The boronic acid D can be obtained through a Miyaura borylation reaction. By utilizing Suzuki coupling reactions, the boronic acid D can then be either transformed directly into compound F or intermediate E is synthesized first and F can be obtained in a succeeding step in which the Ry-bromo moiety is transformed into the final Rx group. A desilylation reaction leads to intermediate G which is converted into H e.g. via Sonogashira coupling. Finally, compounds of the formula (I) are obtained via deprotection reaction. The products are isolated by conventional means and preferably purified by chromatography.

Scheme I:

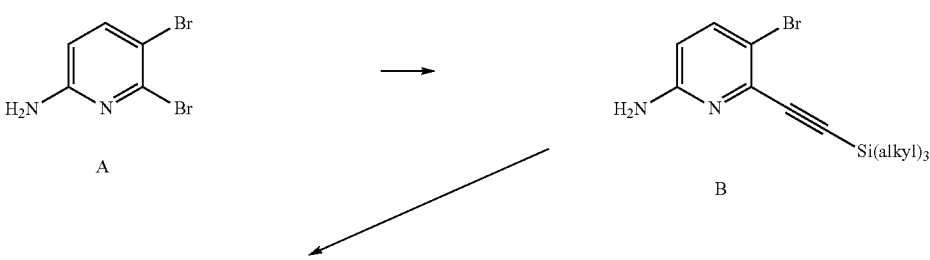

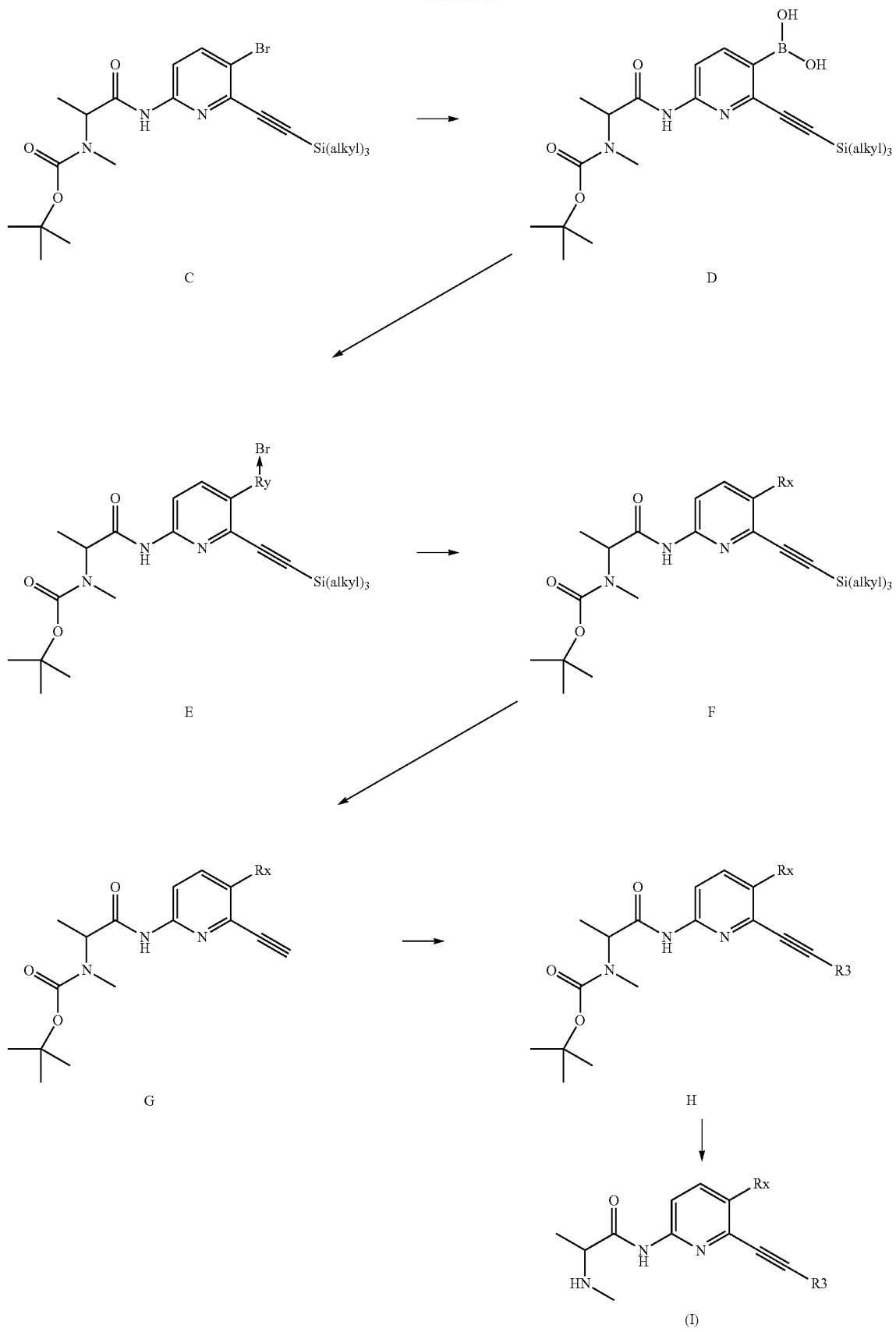

Preparation of Compounds B

B1) 5-bromo-6-[2-tri(propan-2-yl)silylethynyl]pyridin-2-amine

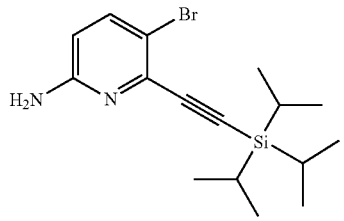 [SMILES: CC(C)[Si](C#Cc1nc(N)ccc1Br)(C(C)C)C(C)C]

Under argon atmosphere a mixture of 5,6-dibromopyridin-2-amine (60 g, 233 mmol), ethynyl-tri(propan-2-yl)silane (64 ml, 285 mmol), copper(I) iodide (1.5 g, 7.88 mmol), triethylamine (80 ml, 577 mmol), ACN (200 ml), THF (100 ml) and dichlorobis(triphenylphosphine)palladium(II) (4.0 g, 5.48 mmol) is stirred for 2 h at 50° C. The solids are filtered off, the mixture is concentrated in vacuo and the product purified by NP chromatography. Yield: 76 g (92%). HPLC-MS: M+H=353/355; tR=1.79 min (Method_1).

Preparation of Compounds C

C1) tert-butyl-N-[1-[[5-bromo-6-[2-tri(propan-2-yl)silylethynyl]pyridin-2-yl]-amino]-1-oxopropan-2-yl]-N-methylcarbamate

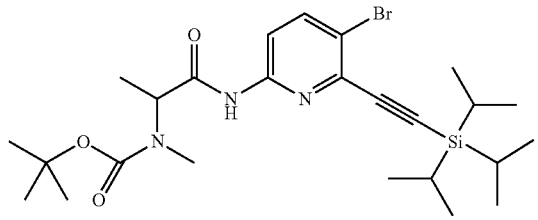 [SMILES: CC(C(=O)Nc1ccc(Br)c(C#C[Si](C(C)C)(C(C)C)C(C)C)n1)N(C)C(=O)OC(C)(C)C]

N,N'-Dicyclohexylcarbodiimide is added portionwise to a mixture of (46.4 g, 225 mmol) 2-[methyl-[(2-methylpropan-2-yl)oxycarbonyl]amino]propanoic acid (72.9 g, 359 mmol) and DCM (200 ml) under stirring at 5° C. This mixture is warmed to RT and stirring continued for 30 minutes before a mixture of 5-bromo-6-[2-tri(propan-2-yl)silylethynyl]-pyridin-2-amine B1 (53 g, 150 mmol) in DCM (200 ml) is added slowly. After stirring for 10 days at RT the mixture is diluted with DCM and extracted with aqueous saturated NaHCO₃. The combined organic layers are dried over MgSO₄ and concentrated in vacuo. The product is purified by NP chromatography. Yield: 71 g (87%). HPLC-MS: M+H=538/540; tR=1.98 min (Method_1).

In order to obtain (R)- or (S)-enantiomers of final examples (2R)-2-[methyl-[(2-methylpropan-2-yl)oxycarbonyl]amino]propanoic acid or (2S)-2-[methyl-[(2-methylpropan-2-yl)oxycarbonyl]amino]propanoic acid can be employed. E.g. with (2S)-2-[methyl-[(2-methylpropan-2-yl)oxycarbonyl]amino]propanoic acid the intermediate tert-butyl N-[(1S)-1-[(5-bromo-6-{2-[tris (propan-2-yl)silyl] ethynyl}pyridin-2-yl)carbamoyl]-ethyl]-N-methylcarbamate is obtained (S)—C1:

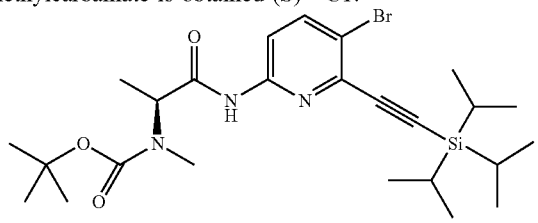

Yield: 71 g (87%). HPLC-MS: M+H=538/540; tR=1.98 min (Method_1).

Accordingly, all subsequent intermediates described below in the racemic form can also be obtained as R- or S-enantiomers. E.g. D1, E1 and F1 are obtained as S-enantiomers starting from (S)—C1 and following the described procedures.

Preparation of Compounds D

D1) [6-[2-[methyl-[(2-methylpropan-2-yl)oxycarbonyl]amino]propanoylamino]-2-[2-tri(propan-2-yl)silylethynyl]pyridin-3-yl]boronic acid

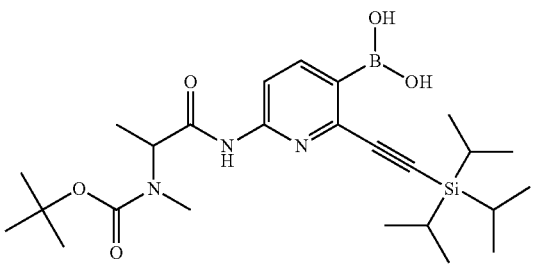 [SMILES: CC(C(=O)Nc1ccc(B(O)O)c(C#C[Si](C(C)C)(C(C)C)C(C)C)n1)N(C)C(=O)OC(C)(C)C]

A mixture of tert-butyl-N-[1-[[5-bromo-6-[2-tri(propan-2-yl)silylethynyl]pyridin-2-yl]-amino]-1-oxopropan-2-yl]-N-methylcarbamate C1 (53 g, 98 mmol), bis(neopentyl glycolato)diboron (44.5 g, 197 mmol), KOAc (29 g, 295 mmol), 1,1'-Bis(diphenylphosphino)ferrocene]dichloropalladium(II) (2.16 g, 2.95 mmol) and dioxane (250 ml) is stirred under argon atmosphere for 7 h at 55° C. The mixture is diluted with DCM and extracted with a saturated aqueous solution of NaHCO₃. The combined organic layers are dried over MgSO₄ and concentrated in vacuo. The product is purified by NP chromatography. Yield: 44 g (89%). HPLC-MS: M+H=504; tR=1.67 min (Method_1).

Preparation of Compounds E

E1) tert-butyl N-{1-[(5-{2-bromo-7-methylimidazo[1,2-a]pyridin-3-yl}-6-{2-[tris(propan-2-yl)silyl]ethynyl}pyridin-2-yl)carbamoyl]ethyl}-N-methylcarbamate

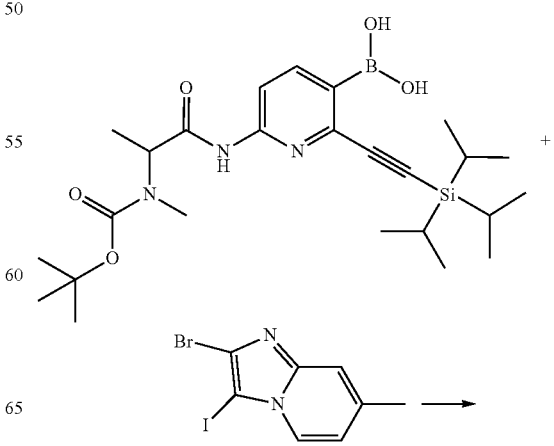

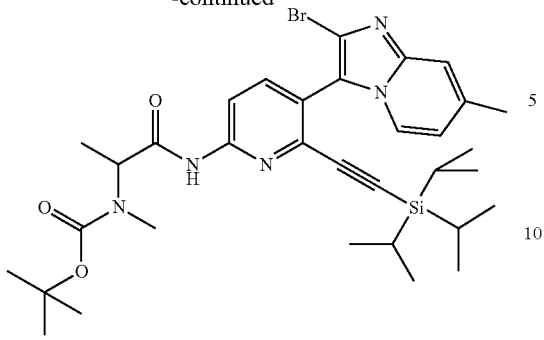

A mixture of [6-[2-[methyl-[(2-methylpropan-2-yl)oxy-carbonyl]amino]propanoylamino]-2-[2-tri(propan-2-yl)silylethynyl]pyridin-3-yl]boronic acid D1 (14.7 g, 29.2 mmol), 2-bromo-3-iodo-7-methylimidazo[1,2-a]pyridine S2 (11.8 g, 35.1 mmol), Na₂CO₃ (9.3 g, 87.7 mmol), dioxane (150 ml), water (30 ml) and 1,1'-bis(diphenylphosphino)ferrocene]dichloropalladium(II) (2.14 g, 2.92 mmol) is stirred under argon atmosphere for 4 h at 110° C. At RT water (100 ml) is added and the mixture extracted with EtOAc. The combined organic layers are dried over MgSO₄, concentrated in vacuo and the product purified by RP HPLC. Yield: 6.9 g (36%). HPLC-MS: M+H=668; tR=1.82 min (Method_1).

Preparation of Compounds F

F1) tert-butyl N-[1-({5-[2-(2-methoxypyridin-3-yl)-7-methylimidazo[1,2-a]pyridin-3-yl]-6-{2-[tris(propan-2-yl)silyl]ethynyl}pyridin-2-yl}carbamoyl)ethyl]-N-methylcarbamate

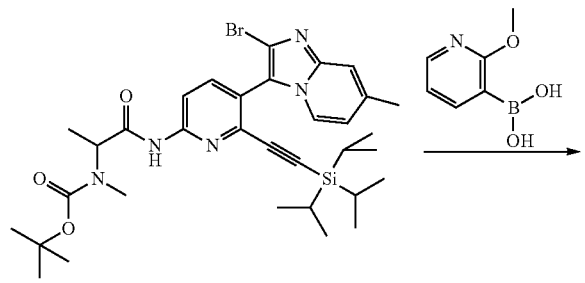

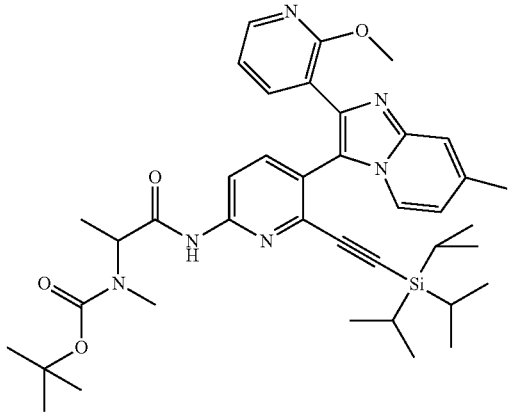

A mixture of tert-butyl N-{1-[(5-{2-bromo-7-methylimidazo[1,2-a]pyridin-3-yl}-6-{2-[tris(propan-2-yl)silyl]ethynyl}pyridin-2-yl)carbamoyl]ethyl}-N-methylcarbamate E1 (1.0 g, 1.50 mmol), (2-methoxypyridin-3-yl)boronic acid (1.0 g, 6.54 mmol), Na₂CO₃ (475 mg, 4.48 mmol), dioxane (10 ml), water (2 ml) and 1,1'-bis(diphenylphosphino)ferrocene]dichloropalladium(II) (218 mg, 298 µmol) is stirred under argon atmosphere for 3 h at 100° C. At RT water (50 ml) is added and the mixture extracted with EtOAc. The combined organic layers are dried over MgSO₄, concentrated in vacuo and the product purified by RP HPLC. Yield: 990 mg (95%). HPLC-MS: M+H=697; tR=2.02 min (Method_4).

The following intermediates are prepared analogously from E1 utilizing corresponding boronic acids (for F2+F5-F9) or boronic acid pinacol esters (for F3-F4):

| # | Structure | Chemical Name | $t_{ret}$ [min] | [M + H] | A.M. |
|---|---|---|---|---|---|
| F2 | 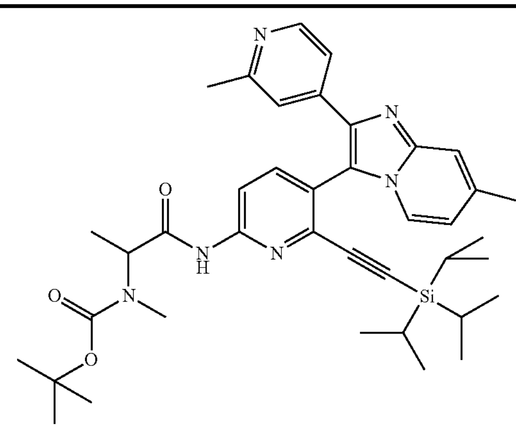 | tert-butyl N-methyl-N-[1-({5-[7-methyl-2-(2-methyl-pyridin-4-yl)imidazo[1,2-a]pyridin-3-yl]-6-{2-[tris(propan-2-yl)silyl]-ethynyl}pyridin-2-yl}carbamoyl)ethyl]carbamate | 1.23 | 681 | M_2 |

| # | Structure | Chemical Name | t_ret [min] | [M + H] | A.M. |
|---|---|---|---|---|---|
| F3 | 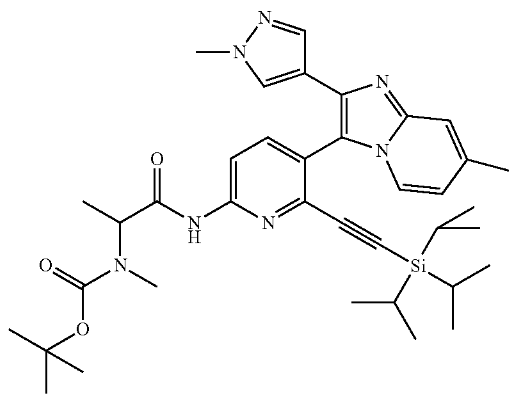 [SMILES: Cc1ccn2c(-c3ccc(NC(=O)C(C)N(C)C(=O)OC(C)(C)C)nc3C#C[Si](C(C)C)(C(C)C)C(C)C)c(-c3cnn(C)c3)nc2c1] | tert-butyl N-methyl-N-[1-({5-[7-methyl-2-(1-methyl-1H-pyrazol-4-yl)imidazo[1,2-a]pyridin-3-yl]-6-{2-[tris(propan-2-yl)silyl]ethynyl}pyridin-2-yl}carbamoyl)ethyl]carbamate | 1.19 | 670 | M_2 |
| F4 | 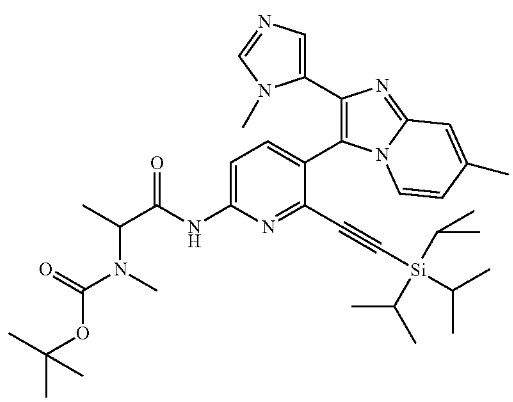 [SMILES: Cc1ccn2c(-c3ccc(NC(=O)C(C)N(C)C(=O)OC(C)(C)C)nc3C#C[Si](C(C)C)(C(C)C)C(C)C)c(-c3cncn3C)nc2c1] | tert-butyl N-methyl-N-[1-({5-[7-methyl-2-(1-methyl-1H-imidazol-5-yl)imidazo[1,2-a]pyridin-3-yl]-6-{2-[tris(propan-2-yl)silyl]ethynyl}pyridin-2-yl}carbamoyl)ethyl]carbamate | 1.19 | 670 | M_2 |
| F5 | 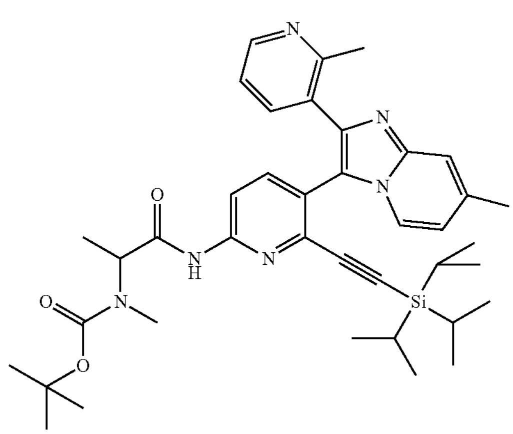 [SMILES: Cc1ccn2c(-c3ccc(NC(=O)C(C)N(C)C(=O)OC(C)(C)C)nc3C#C[Si](C(C)C)(C(C)C)C(C)C)c(-c3cccnc3C)nc2c1] | tert-butyl N-methyl-N-[1-({5-[7-methyl-2-(2-methylpyridin-3-yl)imidazo[1,2-a]pyridin-3-yl]-6-{2-[tris(propan-2-yl)silyl]ethynyl}pyridin-2-yl}carbamoyl)ethyl]carbamate | 1.23 | 681 | M_2 |

| # | Structure | Chemical Name | $t_{ret}$ [min] | [M + H] | A.M. |
|---|---|---|---|---|---|
| F6 | 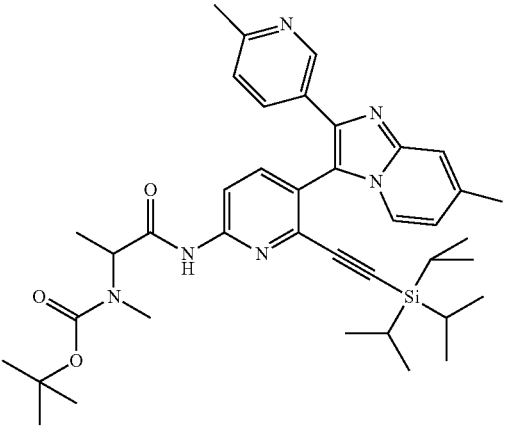 [SMILES: Cc1ccn2c(-c3ccc(NC(=O)C(C)N(C)C(=O)OC(C)(C)C)nc3C#C[Si](C(C)C)(C(C)C)C(C)C)c(-c3ccc(C)nc3)nc2c1] | tert-butyl N-methyl-N-[1-({5-[7-methyl-2-(6-methylpyridin-3-yl)imidazo[1,2-a]pyridin-3-yl]-6-{2-[tris(propan-2-yl)silyl]ethynyl}pyridin-2-yl}carbamoyl)ethyl]carbamate | 1.75 | 681 | M_1 |
| F7 | 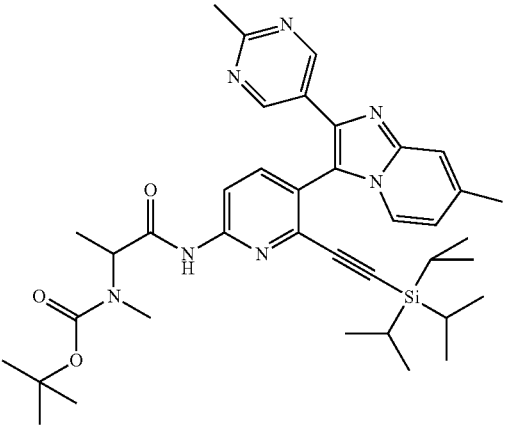 [SMILES: Cc1ccn2c(-c3ccc(NC(=O)C(C)N(C)C(=O)OC(C)(C)C)nc3C#C[Si](C(C)C)(C(C)C)C(C)C)c(-c3cnc(C)nc3)nc2c1] | tert-butyl N-methyl-N-[1-({5-[7-methyl-2-(2-methylpyrimidin-5-yl)imidazo[1,2-a]pyridin-3-yl]-6-{2-[tris(propan-2-yl)silyl]ethynyl}pyridin-2-yl}carbamoyl)ethyl]carbamate | 1.22 | 682 | M_2 |
| F8 | 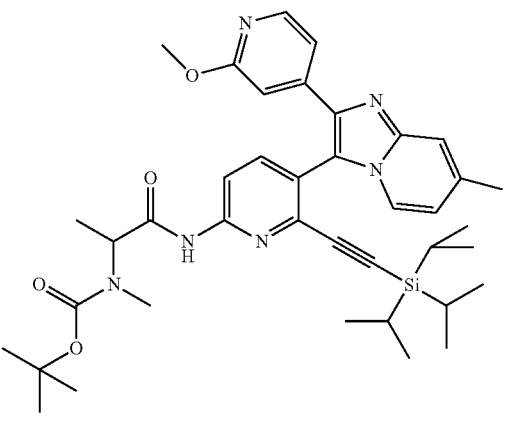 [SMILES: COc1cc(-c2nc3cc(C)ccn3c2-c2ccc(NC(=O)C(C)N(C)C(=O)OC(C)(C)C)nc2C#C[Si](C(C)C)(C(C)C)C(C)C)ccn1] | tert-butyl N-[1-({5-[2-(2-methoxypyridin-4-yl)-7-methylimidazo[1,2-a]pyridin-3-yl]-6-{2-[tris(propan-2-yl)silyl]ethynyl}pyridin-2-yl}carbamoyl)ethyl]-N-methylcarbamate | 2.43 | 697 | M_4 |

-continued

| # | Structure | Chemical Name | $t_{ret}$ [min] | [M + H] | A.M. |
|---|---|---|---|---|---|
| F9 | 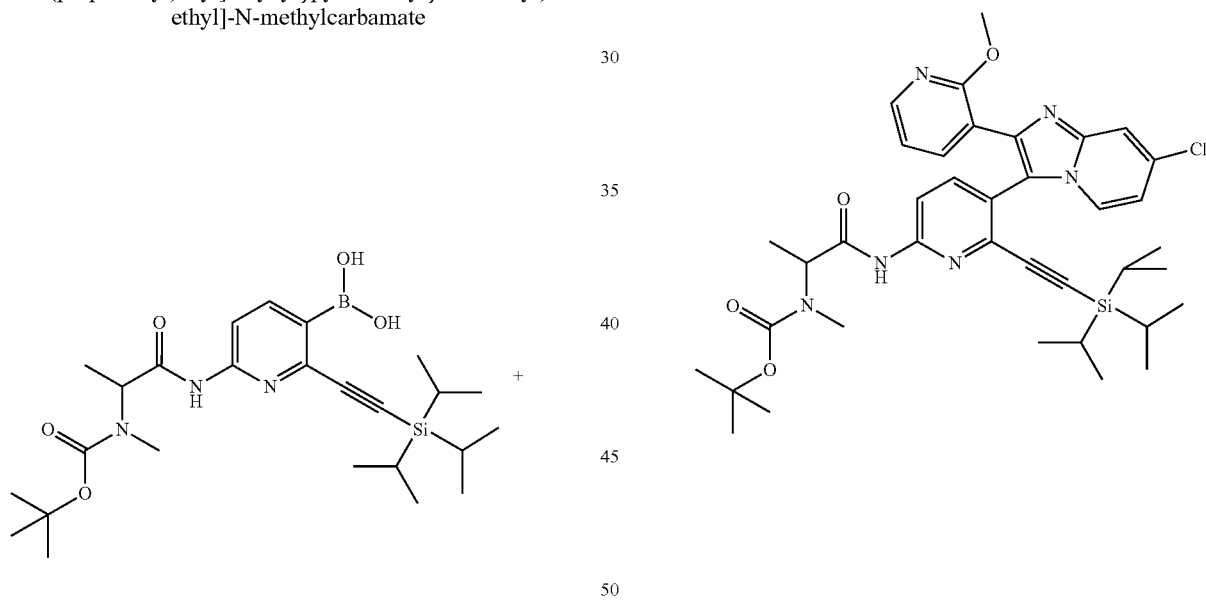 | tert-butyl N-[1-({5-[2-(6-methoxypyridin-3-yl)-7-methylimidazo[1,2-a]pyridin-3-yl]-6-{2-[tris(propan-2-yl)silyl]ethynyl}pyridin-2-yl}carbamoyl)ethyl]-N-methylcarbamate | 1.27 | 697 | M_2 |

F10) tert-butyl N-[1-({5-[7-chloro-2-(2-methoxy-pyridin-3-yl)imidazo[1,2-a]pyridin-3-yl]-6-{2-[tris(propan-2-yl)silyl]ethynyl}pyridin-2-yl}carbamoyl)ethyl]-N-methylcarbamate -continued

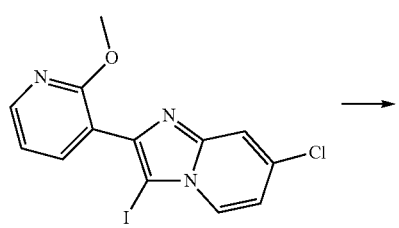

A mixture of [6-[2-[methyl-[(2-methylpropan-2-yl)oxycarbonyl]amino]propanoylamino]-2-[2-tri(propan-2-yl)silylethynyl]pyridin-3-yl]boronic acid D1 (895 mg, 1.78 mmol), 3-{7-chloro-3-iodoimidazo[1,2-a]pyridin-2-yl}-2-methoxypyridine S4a (685 mg, 1.78 mmol), Na₂CO₃ (565 mg, 5.33 mmol), dioxane (8 ml), water (1.5 ml) and 1,1'-bis(diphenylphosphino)ferrocene]dichloropalladium(II) (130 mg, 0.18 mmol) is stirred under argon atmosphere for 3 h at 100° C. At RT water (100 ml) is added and the mixture extracted with EtOAc. The combined organic layers are dried over MgSO₄, concentrated in vacuo and the product purified by RP HPLC. Yield: 480 mg (38%). HPLC-MS: M+H=717; tR=1.30 min (Method_2).

The following intermediate is prepared analogously utilizing S4b:

| # | Structure | Chemical Name | $t_{ret}$ [min] | [M + H] | A.M. |
|---|---|---|---|---|---|
| F11 | 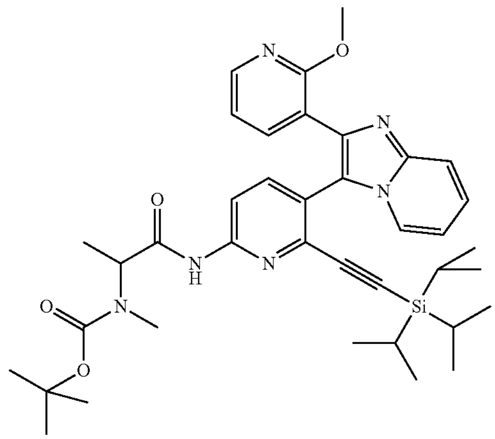 [SMILES: COc1ncccc1-c1nc2ccccn2c1-c1ccc(NC(=O)C(C)N(C)C(=O)OC(C)(C)C)nc1C#C[Si](C(C)C)(C(C)C)C(C)C] | tert-butyl N-[1-({5-[2-(2-methoxypyridin-3-yl)-imidazo[1,2-a]pyridin-3-yl]-6-{2-[tris(propan-2-yl)silyl]ethynyl}pyridin-2-yl}carbamoyl)ethyl]-N-methylcarbamate | 1.25 | 683 | M_2 |

Preparation of Compounds G and H

G1) tert-butyl N-[1-({6-ethynyl-5-[2-(2-methoxy-pyridin-3-yl)-7-methylimidazo[1,2-a]pyridin-3-yl]pyridin-2-yl}carbamoyl)ethyl]-N-methylcarbamate A mixture of tert-butyl N-[1-({5-[2-(2-methoxypyridin-3-yl)-7-methylimidazo[1,2-a]-pyridin-3-yl]-6-{2-[tris(propan-2-yl)silyl]ethynyl}pyridin-2-yl}carbamoyl)ethyl]-N-methylcarbamate F1 (1.1 g, 1.59 mmol), THF (20 ml) and tetrabutylammonium fluoride (1 mol/l solution in THF, 1.8 ml, 1.8 mmol) is stirred at RT for 1 h. The mixture is diluted with EtOAc and extracted with a saturated aqueous solution of sodium hydrogencarbonate and brine. The combined organic layers are dried over MgSO$_4$ and concentrated in vacuo to give crude G1 which is used in the next step without further purification.

H1) tert-butyl N-[1-({5-[2-(2-methoxypyridin-3-yl)-7-methylimidazo[1,2-a]pyridin-3-yl]-6-[2-(1-methylisoquinolin-6-yl)ethynyl]pyridin-2-yl}carbamoyl)ethyl]-N-methylcarbamate

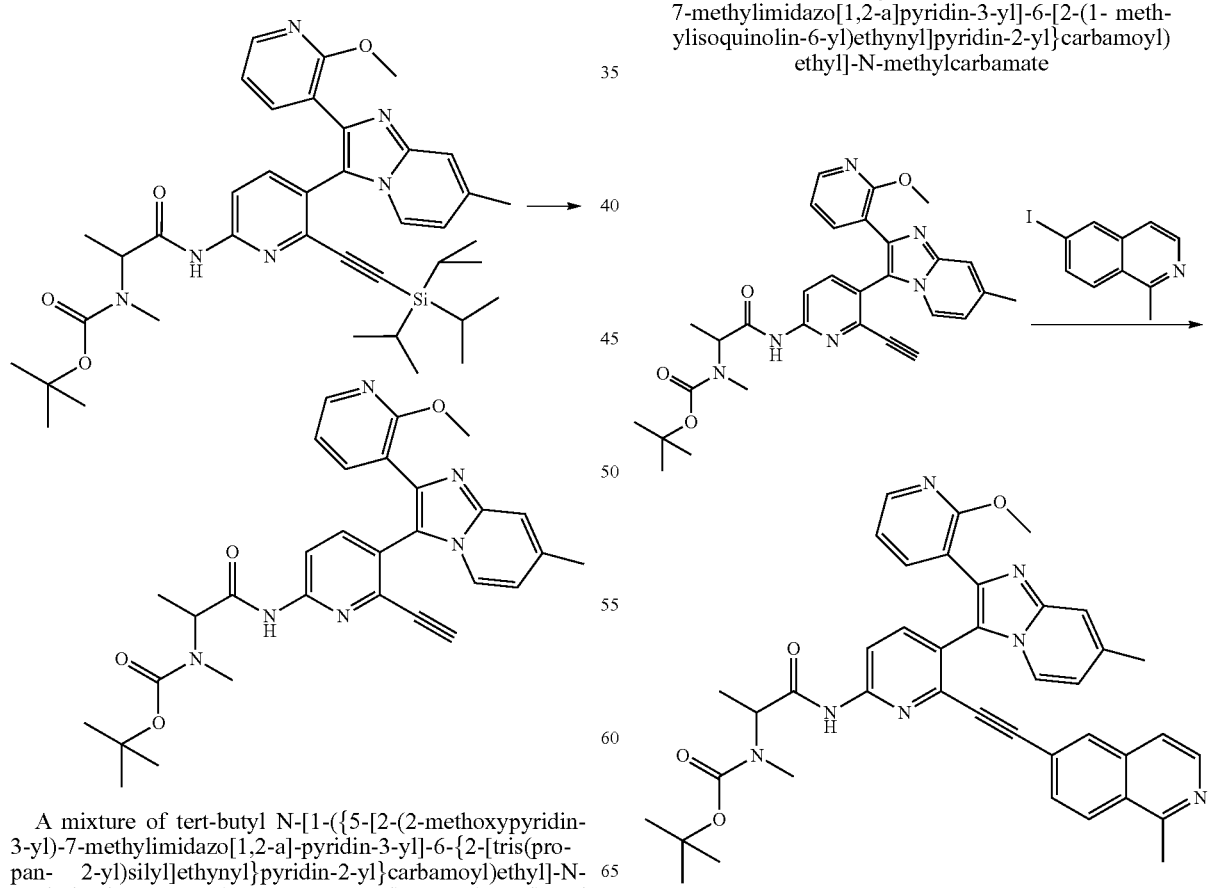

Dichlorobis(triphenylphosphine)palladium(II) (114 mg, 162 µmol) is added to a mixture of tert-butyl N-[1-({6-ethynyl-5-[2-(2-methoxypyridin-3-yl)-7-methylimidazo[1,2-a]pyridin-3-yl]pyridin-2-yl}carbamoyl)ethyl]-N-methyl-carbamate G1 (439 mg, 812 µmol), 6-iodo-1-methylisoquinoline S5 (437 mg, 1.62 mmol), copper(I) iodide (15 mg, 79 µmol), triethylamine (350 µl, 2 mmol) and NMP (2 ml) under argon atmosphere at RT and is stirred at 50° C. for 17 h. The mixture is concentrated in vacuo and the product purified by RP HPLC. Yield: 223 mg (40%). HPLC-MS: M+H=682; tR=1.00 min (METHOD_2).

The following intermediates are prepared analogously utilizing 6-iodo-1-methylisoquinoline S5, 6-iodo-1-methyl-1,2-dihydroquinolin-2-one or iodobenzene:

| # | Structure | Chemical Name | $t_{ret}$ [min] | [M + H] | A.M. |
|---|---|---|---|---|---|
| H2 | 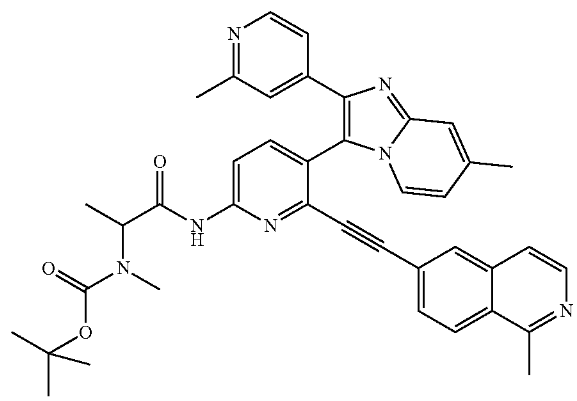 [SMILES: Cc1ccn2c(-c3ccc(NC(=O)C(C)N(C)C(=O)OC(C)(C)C)nc3C#Cc3ccc4c(C)nccc4c3)c(-c3ccnc(C)c3)nc2c1] | tert-butyl N-methyl-N-[1-({5-[7-methyl-2-(2-methylpyridin-4-yl)-imidazo[1,2-a]pyridin-3-yl]-6-[2-(1-methylisoquinolin-6-yl)ethynyl]pyridin-2-yl}carbamoyl)-ethyl]carbamate | 0.98 | 666 | M_2 |
| H3 | 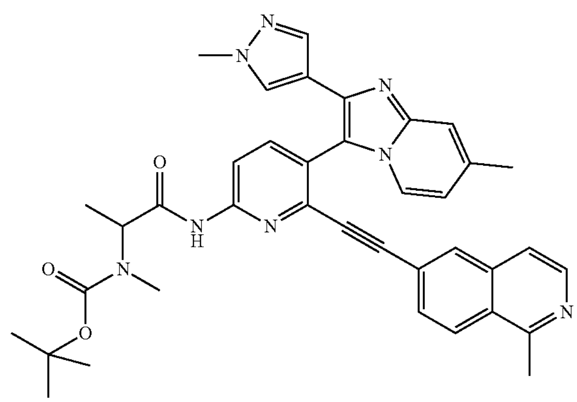 [SMILES: Cc1ccn2c(-c3ccc(NC(=O)C(C)N(C)C(=O)OC(C)(C)C)nc3C#Cc3ccc4c(C)nccc4c3)c(-c3cnn(C)c3)nc2c1] | tert-butyl N-methyl-N-[1-({5-[7-methyl-2-(1-methyl-1H-pyrazol-4-yl)imidazo[1,2-a]-pyridin-3-yl]-6-[2-(1-methylisoquinolin-6-yl)ethynyl]pyridin-2-yl}carbamoyl)-ethyl]carbamate | 0.95 | 655 | M_2 |
| H4 | 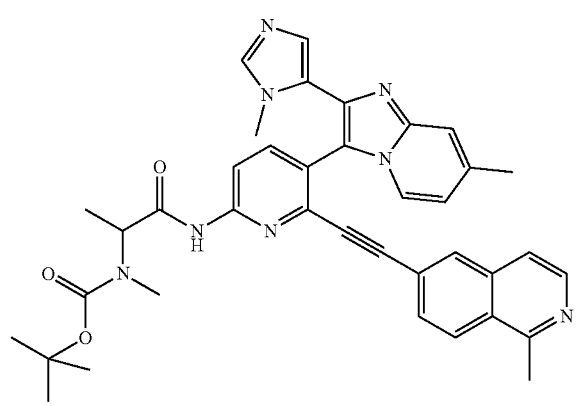 [SMILES: Cc1ccn2c(-c3ccc(NC(=O)C(C)N(C)C(=O)OC(C)(C)C)nc3C#Cc3ccc4c(C)nccc4c3)c(-c3cncn3C)nc2c1] | tert-butyl N-methyl-N-[1-({5-[7-methyl-2-(1-methyl-1H-imidazol-5-yl)imidazo[1,2-a]-pyridin-3-yl]-6-[2-(1-methylisoquinolin-6-yl)ethynyl]pyridin-2-yl}carbamoyl)-ethyl]carbamate | 0.93 | 655 | M_2 |

| # | Structure | Chemical Name | t_ret [min] | [M + H] | A.M. |
|---|-----------|---------------|-------------|---------|------|
| H5 | 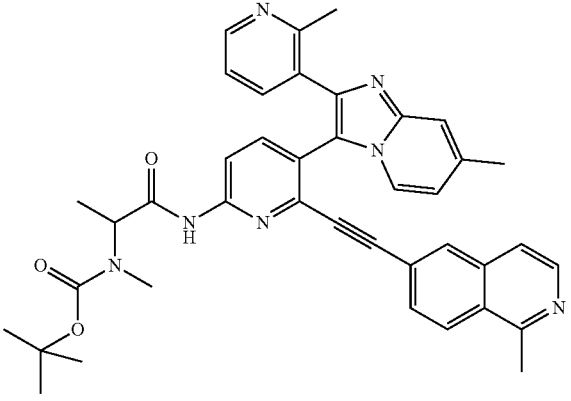 [SMILES: Cc1ccn2c(-c3ccc(NC(=O)C(C)N(C)C(=O)OC(C)(C)C)nc3C#Cc3ccc4c(C)nccc4c3)c(-c3cccnc3C)nc2c1] | tert-butyl N-methyl-N-[1-({5-[7-methyl-2-(2-methylpyridin-3-yl)-imidazo[1,2-a]pyridin-3-yl]-6-[2-(1-methylisoquinolin-6-yl)ethynyl]pyridin-2-yl}carbamoyl)-ethyl]carbamate | 0.96 | 666 | M_2 |
| H6 | 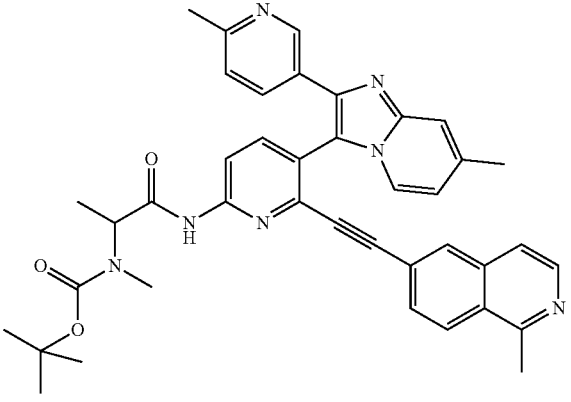 [SMILES: Cc1ccn2c(-c3ccc(NC(=O)C(C)N(C)C(=O)OC(C)(C)C)nc3C#Cc3ccc4c(C)nccc4c3)c(-c3ccc(C)nc3)nc2c1] | tert-butyl N-methyl-N-[1-({5-[7-methyl-2-(6-methylpyridin-3-yl)-imidazo[1,2-a]pyridin-3-yl]-6-[2-(1-methylisoquinolin-6-yl)ethynyl]pyridin-2-yl}carbamoyl)-ethyl]carbamate | 0.99 | 666 | M_2 |
| H7 | 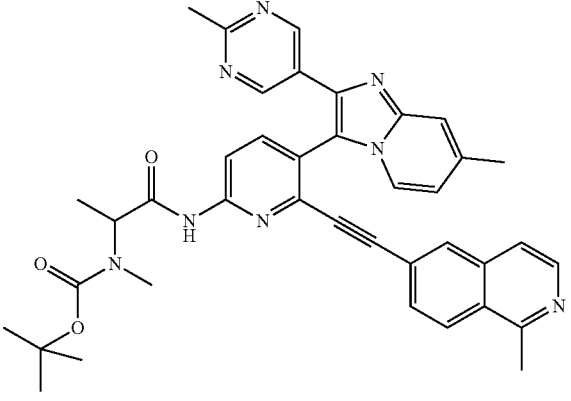 [SMILES: Cc1ccn2c(-c3ccc(NC(=O)C(C)N(C)C(=O)OC(C)(C)C)nc3C#Cc3ccc4c(C)nccc4c3)c(-c3cnc(C)nc3)nc2c1] | tert-butyl N-methyl-N-[1-({5-[7-methyl-2-(2-methylpyrimidin-5-yl)imidazo[1,2-a]-pyridin-3-yl]-6-[2-(1-methylisoquinolin-6-yl)ethynyl]pyridin-2-yl}carbamoyl)-ethyl]carbamate | 0.96 | 667 | M_2 |

-continued

| # | Structure | Chemical Name | t_ret [min] | [M + H] | A.M. |
|---|---|---|---|---|---|
| H8 | 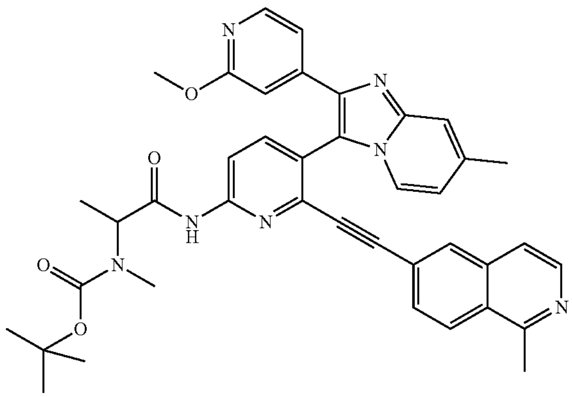 [SMILES: COc1cc(-c2nc3cc(C)ccn3c2-c2ccc(NC(=O)C(C)N(C)C(=O)OC(C)(C)C)nc2C#Cc2ccc3c(C)nccc3c2)ccn1] | tert-butyl N-[1-({5-[2-(2-methoxypyridin-4-yl)-7-methylimidazo[1,2-a]-pyridin-3-yl]-6-[2-(1-methylisoquinolin-6-yl)ethynyl]pyridin-2-yl}carbamoyl)ethyl]-N-methylcarbamate | 1.02 | 682 | M_2 |
| H9 | 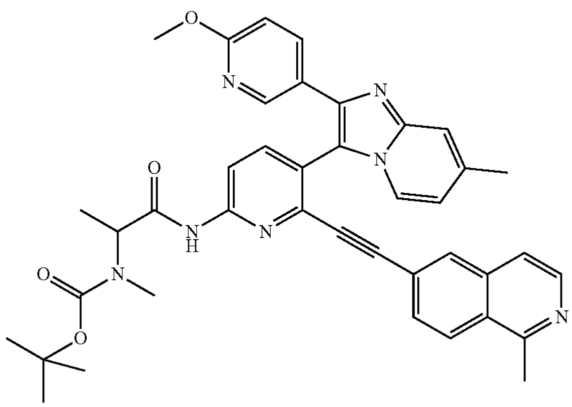 [SMILES: COc1ccc(-c2nc3cc(C)ccn3c2-c2ccc(NC(=O)C(C)N(C)C(=O)OC(C)(C)C)nc2C#Cc2ccc3c(C)nccc3c2)cn1] | tert-butyl N-[1-({5-[2-(6-methoxypyridin-3-yl)-7-methylimidazo[1,2-a]-pyridin-3-yl]-6-[2-(1-methylisoquinolin-6-yl)ethynyl]pyridin-2-yl}carbamoyl)ethyl]-N-methylcarbamate | 1.03 | 682 | M_2 |
| H10 | 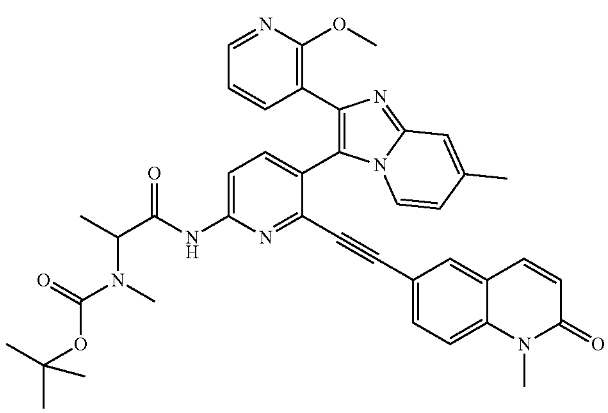 [SMILES: COc1ncccc1-c1nc2cc(C)ccn2c1-c1ccc(NC(=O)C(C)N(C)C(=O)OC(C)(C)C)nc1C#Cc1ccc2c(ccc(=O)n2C)c1] | tert-butyl N-[1-({5-[2-(2-methoxypyridin-3-yl)-7-methyl-imidazo[1,2-a]pyridin-3-yl]-6-[2-(1-methyl-2-oxo-1,2-dihydroquinolin-6-yl)-ethynyl]pyridin-2-yl}-carbamoyl)ethyl]-N-methylcarbamate | 0.96 | 698 | M_2 |

-continued

| # | Structure | Chemical Name | $t_{ret}$ [min] | [M + H] | A.M. |
|---|---|---|---|---|---|
| H11 | 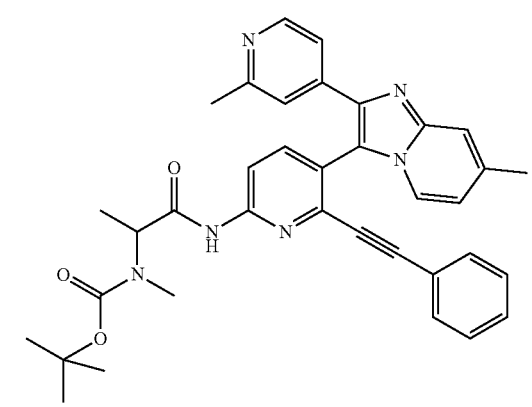 [SMILES: Cc1ccn2c(-c3ccc(NC(=O)C(C)N(C)C(=O)OC(C)(C)C)nc3C#Cc3ccccc3)c(-c3ccnc(C)c3)nc2c1] | tert-butyl N-methyl-N-[1-({5-[7-methyl-2-(2-methylpyridin-4-yl)-imidazo[1,2-a]pyridin-3-yl]-6-(2-phenyl-ethynyl)pyridin-2-yl}-carbamoyl)-ethyl]carbamate | 1.02 | 601 | M_2 |
| H12 | 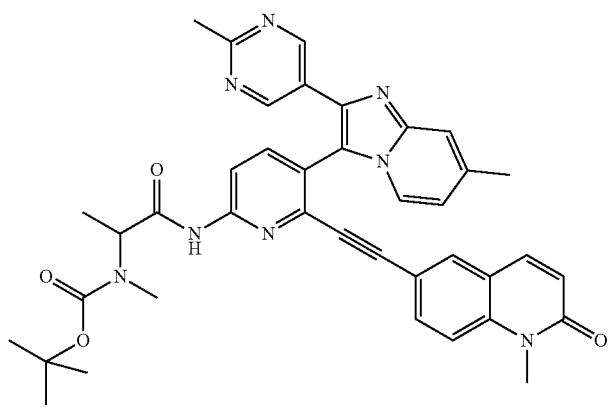 [SMILES: Cc1ccn2c(-c3ccc(NC(=O)C(C)N(C)C(=O)OC(C)(C)C)nc3C#Cc3ccc4c(ccc(=O)n4C)c3)c(-c3cnc(C)nc3)nc2c1] | tert-butyl N-methyl-N-[1-({5-[7-methyl-2-(2-methylpyrimidin-5-yl)imidazo[1,2-a]-pyridin-3-yl]-6-[2-(1-methyl-2-oxo-1,2-dihydroquinolin-6-yl)-ethynyl]pyridin-2-yl}-carbamoyl)-ethyl]carbamate | 0.92 | 683 | M_2 |
| H13 | 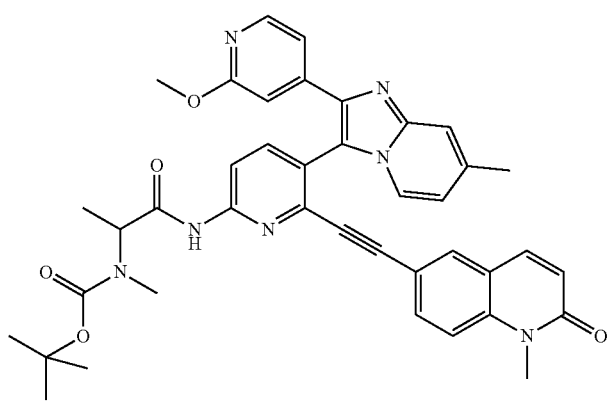 [SMILES: COc1cc(-c2nc3cc(C)ccn3c2-c2ccc(NC(=O)C(C)N(C)C(=O)OC(C)(C)C)nc2C#Cc2ccc3c(ccc(=O)n3C)c2)ccn1] | tert-butyl N-[1-({5-[2-(2-methoxypyridin-4-yl)-7-methylimidazo[1,2-a]-pyridin-3-yl]-6-[2-(1-methyl-2-oxo-1,2-dihydroquinolin-6-yl)-ethynyl]pyridin-2-yl}-carbamoyl)ethyl]-N-methylcarbamate | 0.98 | 698 | M_2 |

-continued

| # | Structure | Chemical Name | t_ret [min] | [M + H] | A.M. |
|---|---|---|---|---|---|
| H14 | 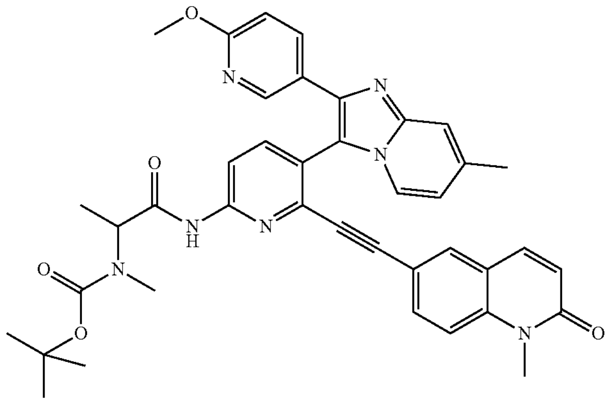 [SMILES: COc1ccc(-c2nc3cc(C)ccn3c2-c2ccc(NC(=O)C(C)N(C)C(=O)OC(C)(C)C)nc2C#Cc2ccc3c(ccc(=O)n3C)c2)cn1] | tert-butyl N-[1-({5-[2-(6-methoxypyridin-3-yl)-7-methylimidazo[1,2-a]-pyridin-3-yl]-6-[2-(1-methyl-2-oxo-1,2-dihydroquinolin-6-yl)-ethynyl]pyridin-2-yl}-carbamoyl)ethyl]-N-methylcarbamate | 0.99 | 698 | M_2 |
| H15 | 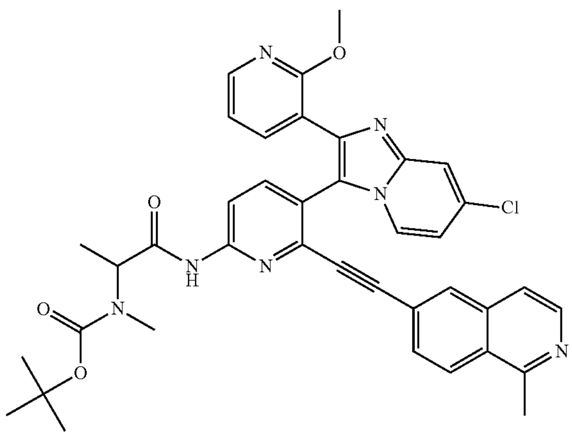 [SMILES: COc1ncccc1-c1nc2cc(Cl)ccn2c1-c1ccc(NC(=O)C(C)N(C)C(=O)OC(C)(C)C)nc1C#Cc1ccc2c(C)nccc2c1] | tert-butyl N-[1-({5-[7-chloro-2-(2-methoxypyridin-3-yl)-imidazo[1,2-a]pyridin-3-yl]-6-[2-(1-methylisoquinolin-6-yl)ethynyl]pyridin-2-yl}carbamoyl)ethyl]-N-methylcarbamate | 1.04 | 702 | M_2 |
| H16 | 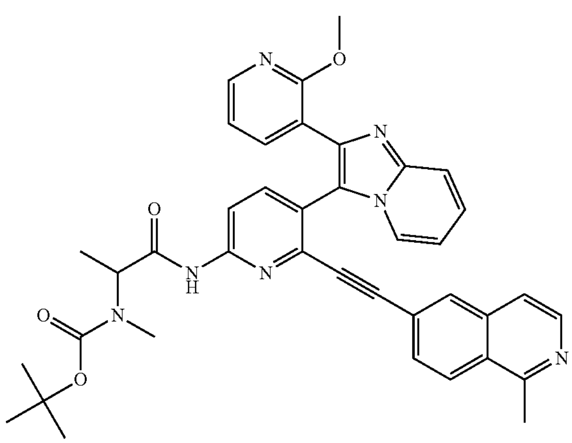 [SMILES: COc1ncccc1-c1nc2ccccn2c1-c1ccc(NC(=O)C(C)N(C)C(=O)OC(C)(C)C)nc1C#Cc1ccc2c(C)nccc2c1] | tert-butyl N-[1-({5-[2-(2-methoxypyridin-3-yl)imidazo[1,2-a]-pyridin-3-yl]-6-[2-(1-methylisoquinolin-6-yl)ethynyl]pyridin-2-yl}carbamoyl)ethyl]-N-methylcarbamate | 0.98 | 668 | M_2 |

Preparation of Examples (I)

Example 1

N-{5-[2-(2-methoxypyridin-3-yl)-7-methylimidazo[1,2-a]pyridin-3-yl]-6-[2-(1-methylisoquinolin-6-yl)ethynyl]pyridin-2-yl}-2-(methylamino)propanamide

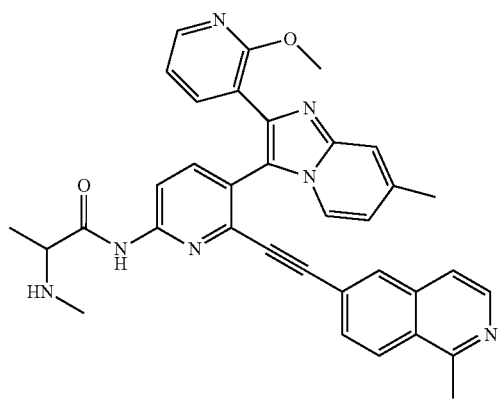 [SMILES: CNC(C)C(=O)Nc1ccc(-c2c(-c3cccnc3OC)nc3cc(C)ccn23)c(C#Cc2ccc3c(C)nccc3c2)n1]

A mixture of tert-butyl N-[1-({5-[2-(2-methoxypyridin-3-yl)-7-methylimidazo[1,2-a]-pyridin-3-yl]-6-[2-(1-methyl-isoquinolin-6-yl)ethynyl]pyridin-2-yl}carbamoyl)ethyl]-N-methylcarbamate H1 (223 mg, 327 µmol), DCM (10 ml) and TFA (2 ml) is stirred for 1 h at RT. Toluene (50 ml) is added and the mixture concentrated in vacuo. The product is purified by RP HPLC. Yield: 88 mg (46%). HPLC-MS: M+H=582; tR=1.17 min (METHOD_1).

The following examples are prepared analogously from H2-H16:

| # | Structure | Chemical Name | $t_{ret}$ [min] | [M + H] | A.M. |
|---|---|---|---|---|---|
| 2 | 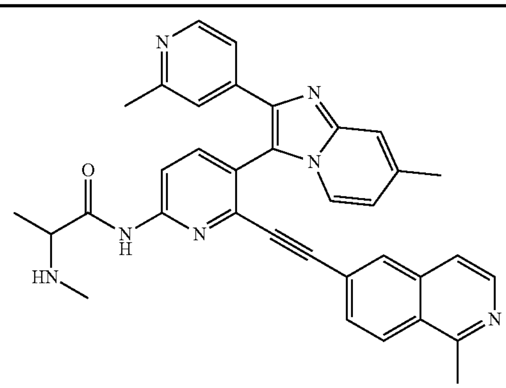 | N-{5-[7-methyl-2-(2-methylpyridin-4-yl)-imidazo[1,2-a]pyridin-3-yl]-6-[2-(1-methyl-isoquinolin-6-yl)-ethynyl]pyridin-2-yl}-2-(methylamino)-propanamide | 1.13 | 566 | M_1 |
| 3 | 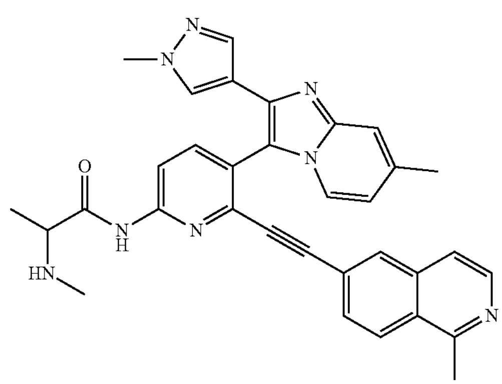 [SMILES: CNC(C)C(=O)Nc1ccc(-c2c(-c3cnn(C)c3)nc3cc(C)ccn23)c(C#Cc2ccc3c(C)nccc3c2)n1] | N-{5-[7-methyl-2-(1-methyl-1H-pyrazol-4-yl)imidazo[1,2-a]-pyridin-3-yl]-6-[2-(1-methylisoquinolin-6-yl)ethynyl]pyridin-2-yl}-2-(methylamino)-propanamide | 1.10 | 555 | M_1 |

| # | Structure | Chemical Name | t_ret [min] | [M + H] | A.M. |
|---|---|---|---|---|---|
| 4 | 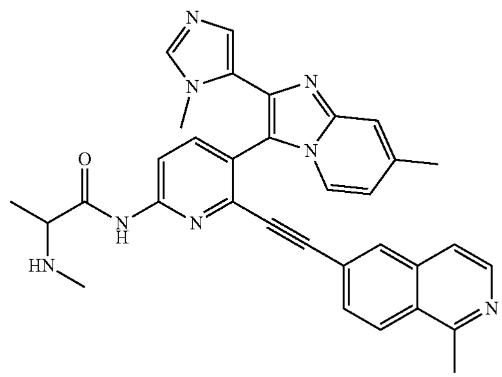 [SMILES: CNC(C)C(=O)Nc1ccc(-c2c(-c3cncn3C)nc3cc(C)ccn23)c(C#Cc2ccc3c(C)nccc3c2)n1] | N-{5-[7-methyl-2-(1-methyl-1H-imidazol-5-yl)imidazo[1,2-a]-pyridin-3-yl]-6-[2-(1-methylisoquinolin-6-yl)ethynyl]pyridin-2-yl}-2-(methylamino)-propanamide | 1.09 | 555 | M_1 |
| 5 | 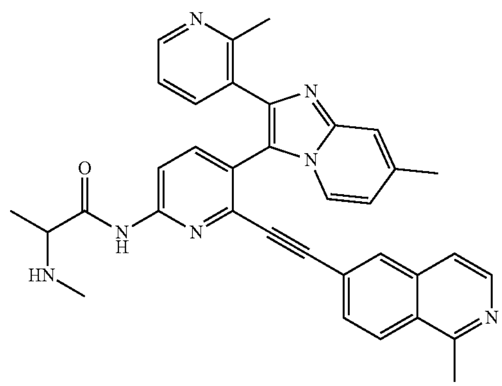 [SMILES: CNC(C)C(=O)Nc1ccc(-c2c(-c3cccnc3C)nc3cc(C)ccn23)c(C#Cc2ccc3c(C)nccc3c2)n1] | N-{5-[7-methyl-2-(2-methylpyridin-3-yl)-imidazo[1,2-a]pyridin-3-yl]-6-[2-(1-methyl-isoquinolin-6-yl)-ethynyl]pyridin-2-yl}-2-(methylamino)-propanamide | 1.12 | 566 | M_1 |
| 6 | 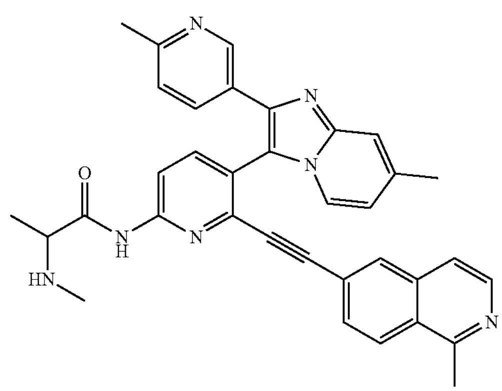 [SMILES: CNC(C)C(=O)Nc1ccc(-c2c(-c3ccc(C)nc3)nc3cc(C)ccn23)c(C#Cc2ccc3c(C)nccc3c2)n1] | N-{5-[7-methyl-2-(6-methylpyridin-3-yl)-imidazo[1,2-a]pyridin-3-yl]-6-[2-(1-methyl-isoquinolin-6-yl)-ethynyl]pyridin-2-yl}-2-(methylamino)-propanamide | 1.14 | 566 | M_1 |
| 7 | 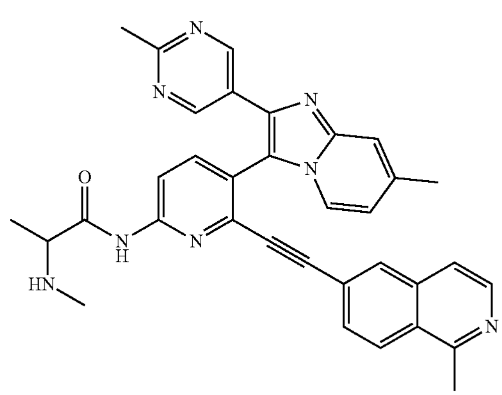 [SMILES: CNC(C)C(=O)Nc1ccc(-c2c(-c3cnc(C)nc3)nc3cc(C)ccn23)c(C#Cc2ccc3c(C)nccc3c2)n1] | N-{5-[7-methyl-2-(2-methylpyrimidin-5-yl)imidazo[1,2-a]-pyridin-3-yl]-6-[2-(1-methylisoquinolin-6-yl)ethynyl]pyridin-2-yl}-2-(methylamino)-propanamide | 1.12 | 567 | M_1 |

-continued

| # | Structure | Chemical Name | t_ret [min] | [M + H] | A.M. |
|---|---|---|---|---|---|
| 8 | 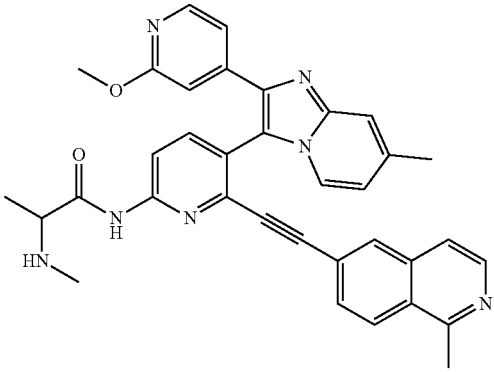 [SMILES: CNC(C)C(=O)Nc1ccc(-c2c(-c3ccnc(OC)c3)nc3cc(C)ccn23)c(C#Cc2ccc3c(C)nccc3c2)n1] | N-{5-[2-(2-methoxypyridin-4-yl)-7-methylimidazo[1,2-a]pyridin-3-yl]-6-[2-(1-methylisoquinolin-6-yl)ethynyl]pyridin-2-yl}-2-(methylamino)propanamide | 1.21 | 582 | M_1 |
| 9 | 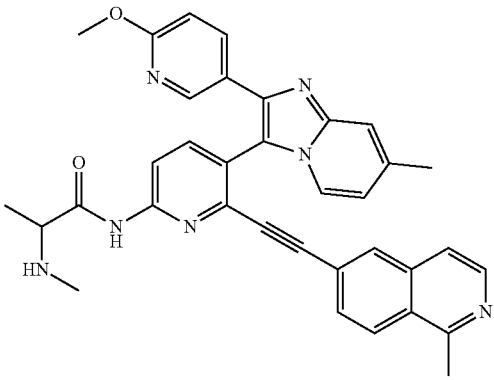 [SMILES: CNC(C)C(=O)Nc1ccc(-c2c(-c3ccc(OC)nc3)nc3cc(C)ccn23)c(C#Cc2ccc3c(C)nccc3c2)n1] | N-{5-[2-(6-methoxypyridin-3-yl)-7-methylimidazo[1,2-a]pyridin-3-yl]-6-[2-(1-methylisoquinolin-6-yl)ethynyl]pyridin-2-yl}-2-(methylamino)propanamide | 1.23 | 582 | M_1 |
| 10 | 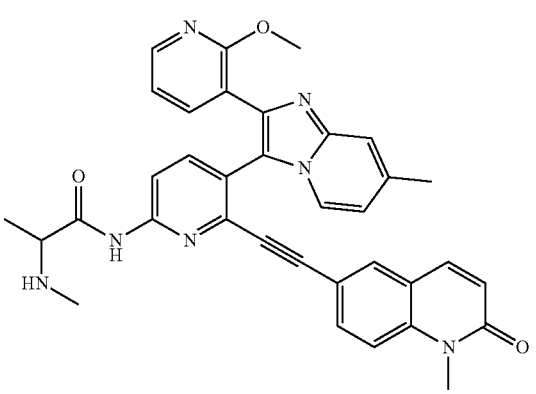 [SMILES: CNC(C)C(=O)Nc1ccc(-c2c(-c3cccnc3OC)nc3cc(C)ccn23)c(C#Cc2ccc3c(ccc(=O)n3C)c2)n1] | N-{5-[2-(2-methoxypyridin-3-yl)-7-methylimidazo[1,2-a]-pyridin-3-yl]-6-[2-(1-methyl-2-oxo-1,2-dihydroquinolin-6-yl)-ethynyl]pyridin-2-yl}-2-(methylamino)-propanamide | 1.10 | 598 | M_1 |
| 11 | 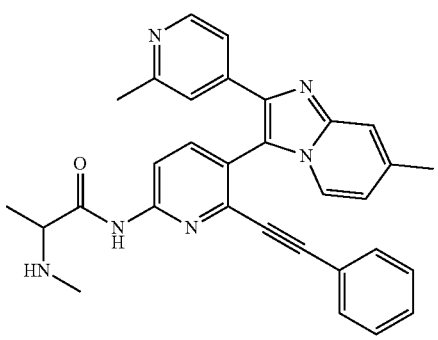 [SMILES: CNC(C)C(=O)Nc1ccc(-c2c(-c3ccnc(C)c3)nc3cc(C)ccn23)c(C#Cc2ccccc2)n1] | N-{5-[7-methyl-2-(2-methylpyridin-4-yl)-imidazo[1,2-a]pyridin-3-yl]-6-(2-phenylethynyl)pyridin-2-yl}-2-(methylamino)-propanamide | 1.19 | 501 | M_1 |

| # | Structure | Chemical Name | t_ret [min] | [M + H] | A.M. |
|---|---|---|---|---|---|
| 12 | 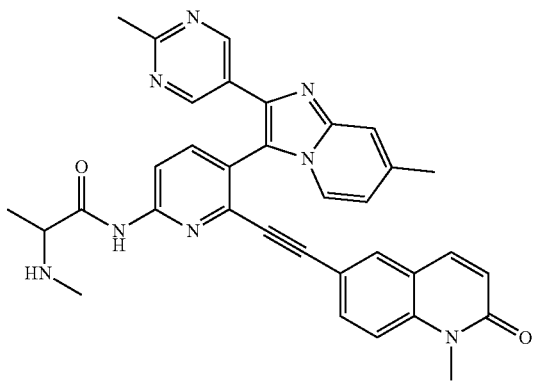 [SMILES: CNC(C)C(=O)Nc1ccc(-c2c(-c3cnc(C)nc3)nc3cc(C)ccn23)c(C#Cc2ccc3c(ccc(=O)n3C)c2)n1] | N-{5-[7-methyl-2-(2-methylpyrimidin-5-yl)imidazo[1,2-a]-pyridin-3-yl]-6-[2-(1-methyl-2-oxo-1,2-dihydroquinolin-6-yl)-ethynyl]pyridin-2-yl}-2-(methylamino)-propanamide | 1.04 | 583 | M_1 |
| 13 | 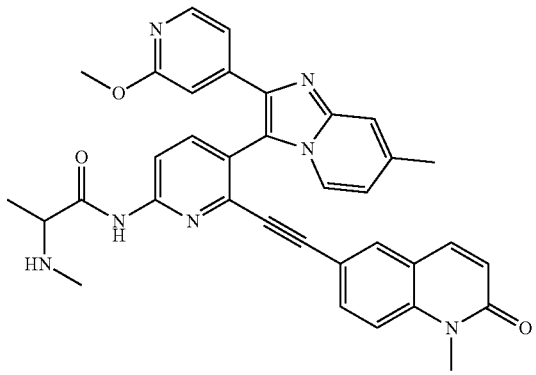 [SMILES: CNC(C)C(=O)Nc1ccc(-c2c(-c3ccnc(OC)c3)nc3cc(C)ccn23)c(C#Cc2ccc3c(ccc(=O)n3C)c2)n1] | N-{5-[2-(2-methoxypyridin-4-yl)-7-methylimidazo[1,2-a]-pyridin-3-yl]-6-[2-(1-methyl-2-oxo-1,2-dihydroquinolin-6-yl)-ethynyl]pyridin-2-yl}-2-(methylamino)-propanamide | 1.13 | 598 | M_1 |
| 14 | 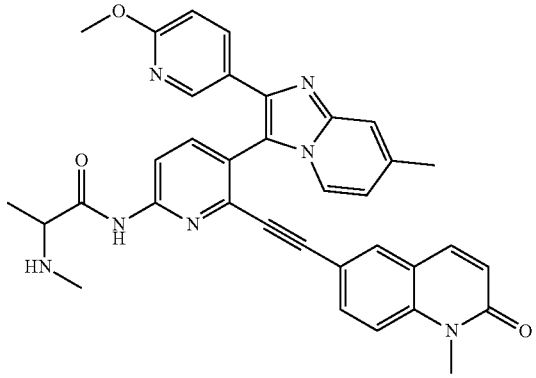 [SMILES: CNC(C)C(=O)Nc1ccc(-c2c(-c3ccc(OC)nc3)nc3cc(C)ccn23)c(C#Cc2ccc3c(ccc(=O)n3C)c2)n1] | N-{5-[2-(6-methoxypyridin-3-yl)-7-methylimidazo[1,2-a]-pyridin-3-yl]-6-[2-(1-methyl-2-oxo-1,2-dihydroquinolin-6-yl)-ethynyl]pyridin-2-yl}-2-(methylamino)-propanamide | 1.15 | 598 | M_1 |
| 15 | 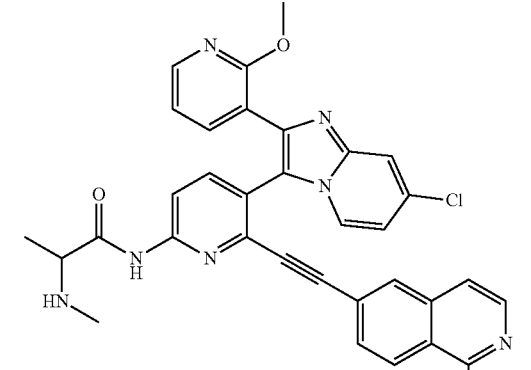 | N-{5-[7-chloro-2-(2-methoxypyridin-3-yl)-imidazo[1,2-a]pyridin-3-yl]-6-[2-(1-methyl-isoquinolin-6-yl)-ethynyl]pyridin-2-yl}-2-(methylamino)-propanamide | 1.22 | 602 | M_1 |

| # | Structure | Chemical Name | $t_{ret}$ [min] | [M + H] | A.M. |
|---|---|---|---|---|---|
| 16 | 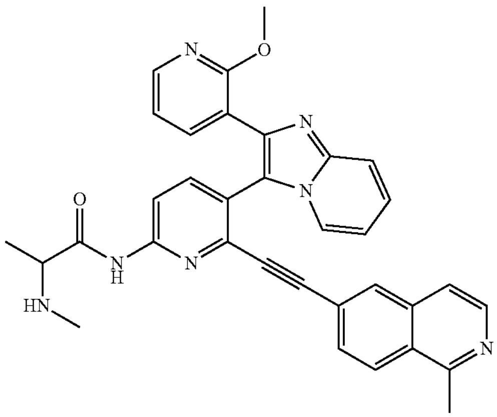 [SMILES: CNC(C)C(=O)Nc1ccc(-c2c(-c3cccnc3OC)nc3ccccn23)c(C#Cc2ccc3c(C)nccc3c2)n1] | N-{5-[2-(2-methoxypyridin-3-yl)imidazo-[1,2-a]pyridin-3-yl]-6-[2-(1-methylisoquinolin-6-yl)ethynyl]-pyridin-2-yl}-2-(methylamino)-propanamide | 1.11 | 508 | M_1 |

The (S)-enantiomers of examples are obtained by employing (S)—C1 instead of C1 in the synthetic route:

| # | Structure | Chemical Name | $t_{ret}$ [min] | [M + H] | A.M. |
|---|---|---|---|---|---|
| (S)-1 | 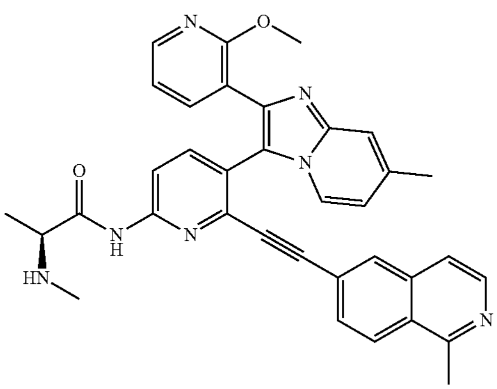 [SMILES: CN[C@@H](C)C(=O)Nc1ccc(-c2c(-c3cccnc3OC)nc3cc(C)ccn23)c(C#Cc2ccc3c(C)nccc3c2)n1] | (2S)-N-{5-[2-(2-methoxypyridin-3-yl)-7-methylimidazo[1,2-a]pyridin-3-yl]-6-[2-(1-methylisoquinolin-6-yl)ethynyl]pyridin-2-yl}-2-(methylamino)propanamide | 1.17 | 582 | M_1 |
| (S)-2 | 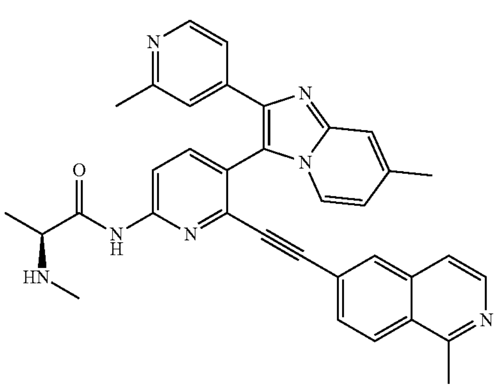 [SMILES: CN[C@@H](C)C(=O)Nc1ccc(-c2c(-c3ccnc(C)c3)nc3cc(C)ccn23)c(C#Cc2ccc3c(C)nccc3c2)n1] | (2S)-N-{5-[7-methyl-2-(2-methylpyridin-4-yl)imidazo[1,2-a]-pyridin-3-yl]-6-[2-(1-methylisoquinolin-6-yl)ethynyl]pyridin-2-yl}-2-(methylamino)-propanamide | 1.13 | 566 | M_1 |

-continued

| # | Structure | Chemical Name | $t_{ret}$ [min] | [M + H] | A.M. |
|---|---|---|---|---|---|
| (S)-3 | 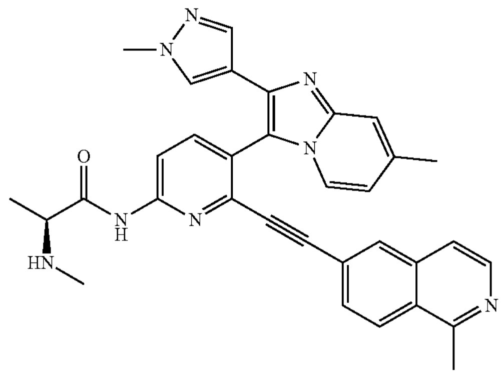 [SMILES: CN[C@@H](C)C(=O)Nc1ccc(-c2c(-c3cnn(C)c3)nc3cc(C)ccn23)c(C#Cc2ccc3c(C)nccc3c2)n1] | (2S)-N-{5-[7-methyl-2-(1-methyl-1H-pyrazol-4-yl)-imidazo[1,2-a]pyridin-3-yl]-6-[2-(1-methyl-isoquinolin-6-yl)-ethynyl]pyridin-2-yl}-2-(methylamino)-propanamide | 1.10 | 555 | M_1 |
| (S)-4 | 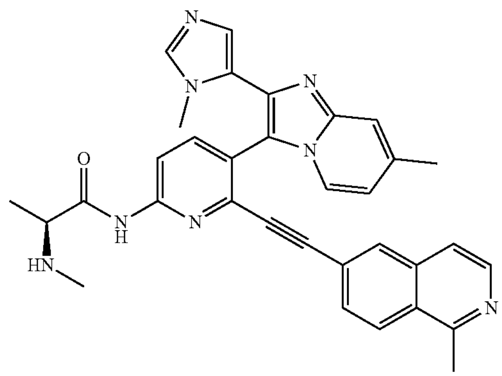 [SMILES: CN[C@@H](C)C(=O)Nc1ccc(-c2c(-c3cncn3C)nc3cc(C)ccn23)c(C#Cc2ccc3c(C)nccc3c2)n1] | (2S)-N-{5-[7-methyl-2-(1-methyl-1H-imidazol-5-yl)-imidazo[1,2-a]pyridin-3-yl]-6-[2-(1-methyl-isoquinolin-6-yl)-ethynyl]pyridin-2-yl}-2-(methylamino)-propanamide | 1.09 | 555 | M_1 |
| (S)-5 | 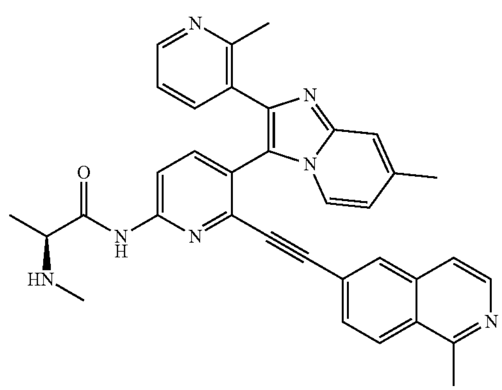 [SMILES: CN[C@@H](C)C(=O)Nc1ccc(-c2c(-c3cccnc3C)nc3cc(C)ccn23)c(C#Cc2ccc3c(C)nccc3c2)n1] | (2S)-N-{5-[7-methyl-2-(2-methylpyridin-3-yl)imidazo[1,2-a]-pyridin-3-yl]-6-[2-(1-methylisoquinolin-6-yl)ethynyl]pyridin-2-yl}-2-(methylamino)-propanamide | 1.12 | 566 | M_1 |
| (S)-6 | 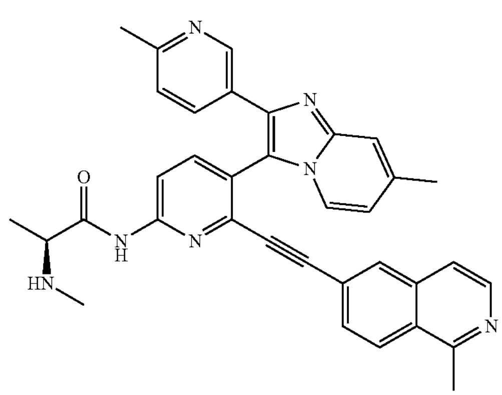 [SMILES: CN[C@@H](C)C(=O)Nc1ccc(-c2c(-c3ccc(C)nc3)nc3cc(C)ccn23)c(C#Cc2ccc3c(C)nccc3c2)n1] | (2S)-N-{5-[7-methyl-2-(6-methylpyridin-3-yl)imidazo[1,2-a]-pyridin-3-yl]-6-[2-(1-methylisoquinolin-6-yl)ethynyl]pyridin-2-yl}-2-(methylamino)-propanamide | 1.14 | 566 | M_1 |

-continued

| # | Structure | Chemical Name | $t_{ret}$ [min] | [M + H] | A.M. |
|---|---|---|---|---|---|
| (S)-7 | 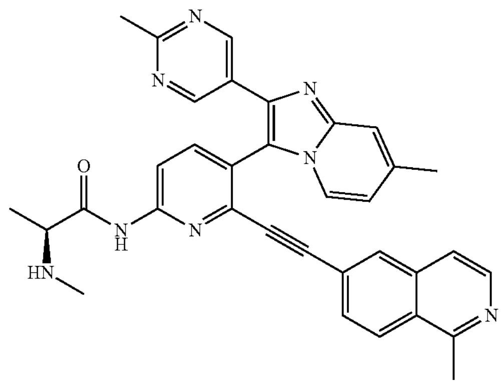 [SMILES: CN[C@@H](C)C(=O)Nc1ccc(-c2c(-c3cnc(C)nc3)nc3cc(C)ccn23)c(C#Cc2ccc3c(C)nccc3c2)n1] | (2S)-N-{5-[7-methyl-2-(2-methylpyrimidin-5-yl)imidazo[1,2-a]pyridin-3-yl]-6-[2-(1-methylisoquinolin-6-yl)ethynyl]pyridin-2-yl}-2-(methylamino)-propanamide | 1.12 | 567 | M_1 |
| (S)-8 | 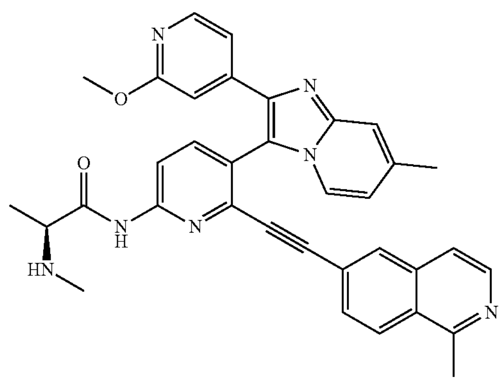 [SMILES: CN[C@@H](C)C(=O)Nc1ccc(-c2c(-c3ccnc(OC)c3)nc3cc(C)ccn23)c(C#Cc2ccc3c(C)nccc3c2)n1] | (2S)-N-{5-[2-(2-methoxypyridin-4-yl)-7-methylimidazo[1,2-a]pyridin-3-yl]-6-[2-(1-methylisoquinolin-6-yl)ethynyl]pyridin-2-yl}-2-(methyl-amino)propanamide | 1.21 | 582 | M_1 |
| (S)-9 | 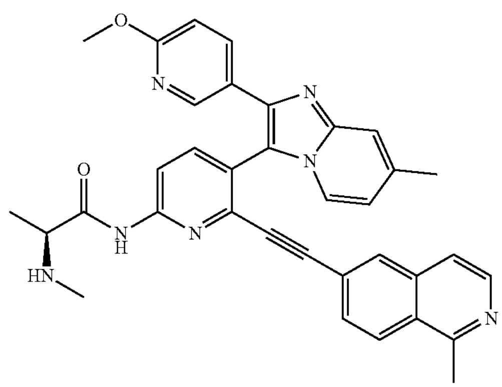 [SMILES: CN[C@@H](C)C(=O)Nc1ccc(-c2c(-c3ccc(OC)nc3)nc3cc(C)ccn23)c(C#Cc2ccc3c(C)nccc3c2)n1] | (2S)-N-{5-[2-(6-methoxypyridin-3-yl)-7-methylimidazo[1,2-a]pyridin-3-yl]-6-[2-(1-methylisoquinolin-6-yl)ethynyl]pyridin-2-yl}-2-(methyl-amino)propanamide | 1.23 | 582 | M_1 |
| (S)-10 | 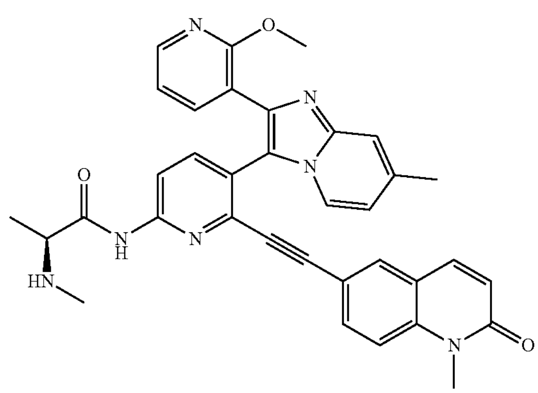 [SMILES: CN[C@@H](C)C(=O)Nc1ccc(-c2c(-c3cccnc3OC)nc3cc(C)ccn23)c(C#Cc2ccc3c(ccc(=O)n3C)c2)n1] | (2S)-N-{5-[2-(2-methoxypyridin-3-yl)-7-methylimidazo[1,2-a]pyridin-3-yl]-6-[2-(1-methyl-2-oxo-1,2-dihydroquinolin-6-yl)-ethynyl]pyridin-2-yl}-2-(methylamino)-propanamide | 1.10 | 598 | M_1 |

| # | Structure | Chemical Name | $t_{ret}$ [min] | [M + H] | A.M. |
|---|---|---|---|---|---|
| (S)-11 | 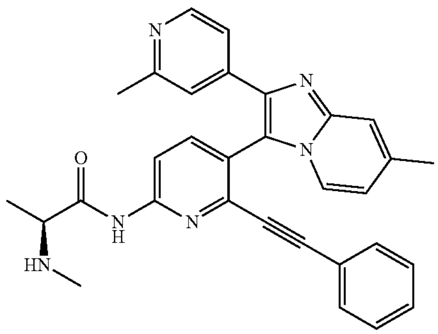 [SMILES: CN[C@@H](C)C(=O)Nc1ccc(-c2c(-c3ccnc(C)c3)nc3cc(C)ccn23)c(C#Cc2ccccc2)n1] | (2S)-N-{5-[7-methyl-2-(2-methylpyridin-4-yl)imidazo[1,2-a]pyridin-3-yl]-6-(2-phenylethynyl)pyridin-2-yl]-2-(methylamino)propanamide | 1.19 | 501 | M_1 |
| (S)-12 | 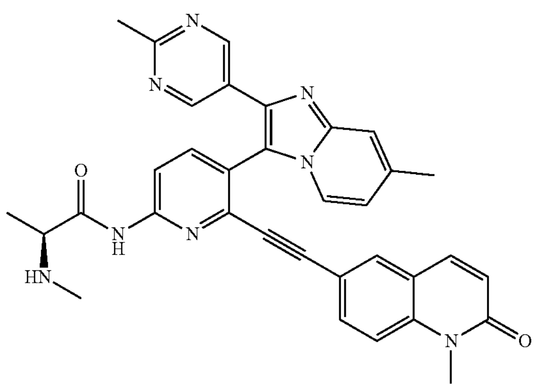 [SMILES: CN[C@@H](C)C(=O)Nc1ccc(-c2c(-c3cnc(C)nc3)nc3cc(C)ccn23)c(C#Cc2ccc3c(ccc(=O)n3C)c2)n1] | (2S)-N-{5-[7-methyl-2-(2-methylpyrimidin-5-yl)imidazo[1,2-a]pyridin-3-yl]-6-[2-(1-methyl-2-oxo-1,2-dihydroquinolin-6-yl)ethynyl]pyridin-2-yl}-2-(methylamino)-propanamide | 1.04 | 583 | M_1 |
| (S)-13 | 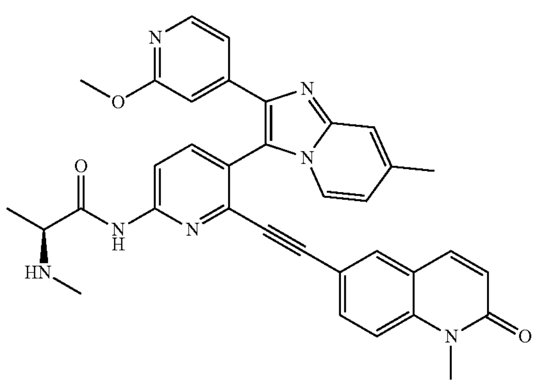 [SMILES: CN[C@@H](C)C(=O)Nc1ccc(-c2c(-c3ccnc(OC)c3)nc3cc(C)ccn23)c(C#Cc2ccc3c(ccc(=O)n3C)c2)n1] | (2S)-N-{5-[2-(2-methoxypyridin-4-yl)-7-methylimidazo[1,2-a]pyridin-3-yl]-6-[2-(1-methyl-2-oxo-1,2-dihydroquinolin-6-yl)ethynyl]pyridin-2-yl}-2-(methylamino)-propanamide | 1.13 | 598 | M_1 |
| (S)-14 | 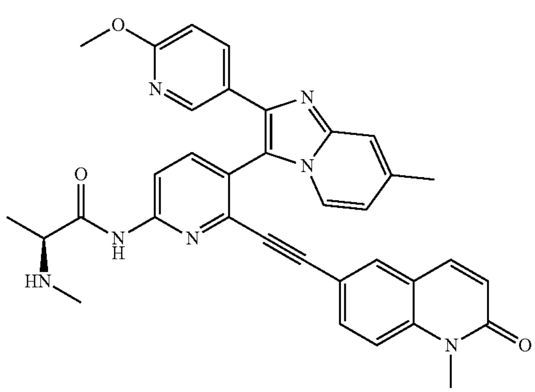 [SMILES: CN[C@@H](C)C(=O)Nc1ccc(-c2c(-c3ccc(OC)nc3)nc3cc(C)ccn23)c(C#Cc2ccc3c(ccc(=O)n3C)c2)n1] | (2S)-N-{5-[5-(6-methoxypyridin-3-yl)-7-methylimidazo[1,2-a]pyridin-3-yl]-6-[2-(1-methyl-2-oxo-1,2-dihydroquinolin-6-yl)ethynyl]pyridin-2-yl}-2-(methylamino)-propanamide | 1.15 | 598 | M_1 |

| # | Structure | Chemical Name | $t_{ret}$ [min] | [M + H] | A.M. |
|---|---|---|---|---|---|
| (S)-15 | 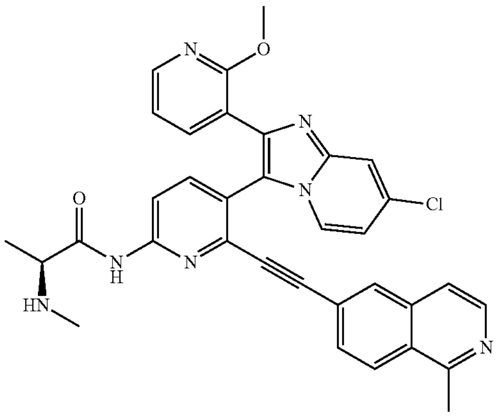 [SMILES: CN[C@@H](C)C(=O)Nc1ccc(-c2c(-c3cccnc3OC)nc3cc(Cl)ccn23)c(C#Cc2ccc3c(C)nccc3c2)n1] | (2S)-N-{5-[7-chloro-2-(2-methoxypyridin-3-yl)imidazo[1,2-a]-pyridin-3-yl]-6-[2-(1-methylisoquinolin-6-yl)ethynyl]pyridin-2-yl}-2-(methylamino)-propanamide | 1.22 | 602 | M_1 |
| (S)-16 | 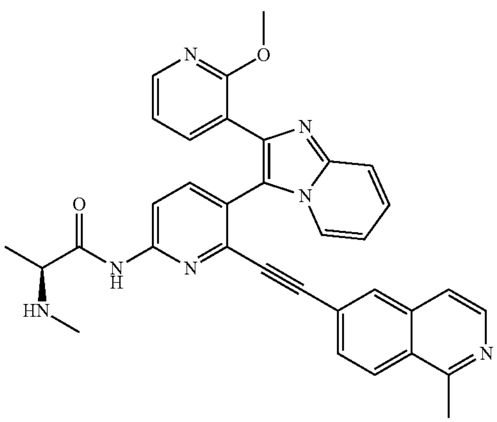 [SMILES: CN[C@@H](C)C(=O)Nc1ccc(-c2c(-c3cccnc3OC)nc3ccccn23)c(C#Cc2ccc3c(C)nccc3c2)n1] | (2S)-N-{5-[5-(2-methoxypyridin-3-yl)imidazo[1,2-a]-pyridin-3-yl]-6-[2-(1-methylisoquinolin-6-yl)ethynyl]pyridin-2-yl}-2-(methylamino)-propanamide | 1.11 | 508 | M_1 |

Preparation of Building Blocks S

S1) 2-bromo-7-methylimidazo[1,2-a]pyridine

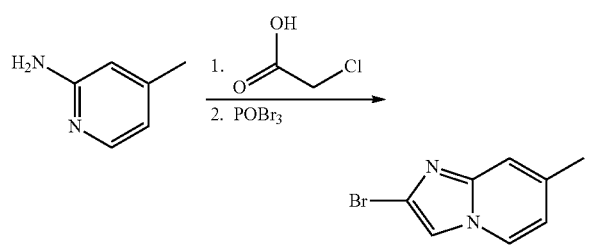

K$_2$CO$_3$ (15.7 g, 114 mmol) is added portionwise to 2-chloroacetic acid (19.6 g, 207 mmol) in water (100 ml) at RT and the mixture stirred for 15 min. 4-Methylpyridin-2-amine (22.5 g, 208 mmol) is added, the mixture heated to reflux for 16 h and cooled to RT. The mixture is concentrated in vacuo to less than half its volume and cold ethanol (200 ml) is added. The precipitate is collected, washed with cold ethanol, dried in vacuo and used directly in the next step.

The crude intermediate and POBr$_3$ (90 g, 341 mmol) are heated to 100° C. for 16 h. The mixture is cooled to RT and slowly added to a cooled stirred mixture of DCM (500 ml) and aqueous NaOH (1 mol/l, 1000 ml). After stirring for 1 h at RT the organic phase is collected and the aqueous layer extracted with DCM. The combined organic layers are dried over MgSO$_4$, concentrated in vacuo and the product purified by NP chromatography. Yield: 8.6 g (20%). HPLC-MS: tR=0.79 min (Method_1).

S2) 2-bromo-3-iodo-7-methylimidazo[1,2-a]pyridine

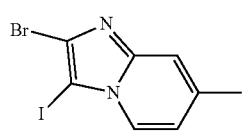

A mixture of 2-bromo-7-methylimidazo[1,2-a]pyridine S1 (8.6 g, 40.8 mmol), N-iodosuccinimide (9.2 g, 40.8 mmol) and ACN (500 ml) is stirred at RT for 3 h. The precipitate is collected, washed with ACN and dried in vacuo. Yield: 11.8 g (86%). HPLC-MS: tR=1.09 min (Method_1)

S3a) 2-chloro-3-{7-chloroimidazo[1,2-a]pyridin-2-yl}pyridine

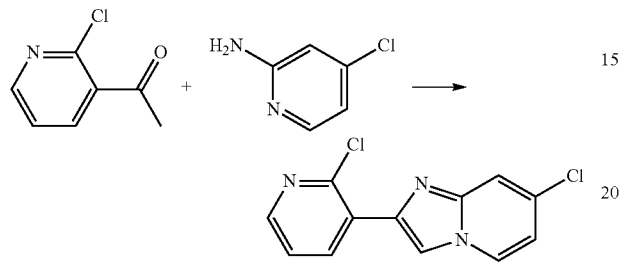

Tetra-N-butylammonium tribromide (3.18 g, 6.60 mmol) is added to 1-(2-chloropyridin-3-yl)ethan-1-one (1 g, 6.43 mmol) in THF (15 ml) at RT and the mixture stirred for 2 h. 4-Chloropyridin-2-amine (0.83 g, 6.43 mmol), NaHCO₃ (0.56 g, 6.67 mmol) and ethanol (10 ml) is added and the mixture stirred at 50° C. for 16 h. At RT water is added and the mixture extracted with EtOAc. The combined organic layers are dried over MgSO₄, concentrated in vacuo and the product purified by RP HPLC. Yield: 0.88 g (52%). HPLC-MS: tR=0.80 min (Method_2).

The following intermediates are prepared analogously:

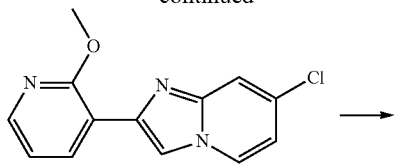

A mixture of 2-chloro-3-{7-chloroimidazo[1,2-a]pyridin-2-yl}pyridine S3a (0.86 g, 3.26 mmol), sodium methoxide (5.4 mol/l in MeOH, 4 ml, 21.6 mmol) and methanol (6 ml) is stirred at 60° C. for 2 days then at 80° C. for 2 days. At RT water is added and the mixture extracted with EtOAc. The combined organic layers are dried over MgSO₄ and concentrated in vacuo. The crude intermediate desiodo-S4a (3-{7-chloroimidazo[1,2-a]pyridin-2-yl}-2-methoxypyridine, HPLC-MS: M+H=260; tR=1.05 min (Method_1) is used directly without further purification).

| # | Structure | Chemical Name | t$_{ret}$ [min] | [M + H] | A.M. |
|---|---|---|---|---|---|
| S3b | 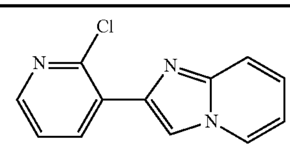 | 2-chloro-3-{imidazo[1,2-a]pyridin-2-yl}pyridine | 0.84 | 230 | M_1 |
| S3c | | 2-chloro-3-{7-methyl-imidazo[1,2-a]pyridin-2-yl}-pyridine | 0.79 | 244 | M_2 |

S4a) 3-{7-chloro-3-iodoimidazo[1,2-a]pyridin-2-yl}-2-methoxypyridine

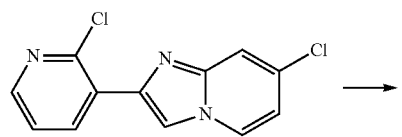

N-iodosuccinimide (0.73 g, 3.26 mmol) and ACN (15 ml) are added to the crude material and the mixture is stirred for 2 h at RT. The precipitate is collected, washed with ACN and dried in vacuo. The filtrate is concentrated in vacuo, EtOAc is added and the mixture washed with an aqueous solution containing 10% sodium thiosulfate. The combined organic layers are dried over MgSO₄, concentrated in vacuo and pooled with the precipitate to give the title compound which is used in the next step without further purification. Yield: 0.69 g (55%). HPLC-MS: M+H=386; tR=1.13 min (Method_1)

The following intermediates are prepared analogously from S3b and S3c:

| # | Structure | Chemical Name | $t_{ret}$ [min] | [M + H] | A.M. |
|---|---|---|---|---|---|
| Desiodo-S4b | 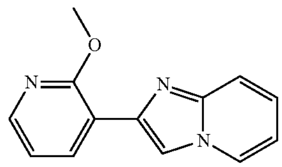 [SMILES: COc1ncccc1-c1cn2ccccc2n1] | 3-{imidazo[1,2-a]-pyridin-2-yl}-2-methoxypyridine | 0.90 | 226 | M_1 |
| S4b | 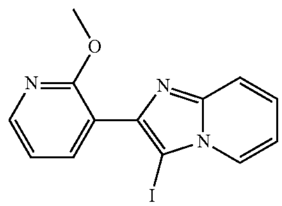 [SMILES: COc1ncccc1-c1nc2ccccn2c1I] | 3-{3-iodoimidazo[1,2-a]-pyridin-2-yl}-2-methoxypyridine | 1.00 | 352 | M_1 |
| Desiodo-S4c | 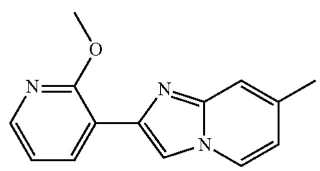 [SMILES: COc1ncccc1-c1cn2ccc(C)cc2n1] | 2-methoxy-3-{7-methylimidazo[1,2-a]pyridin-2-yl}pyridine | 0.81 | 240 | M_2 |
| S4c | 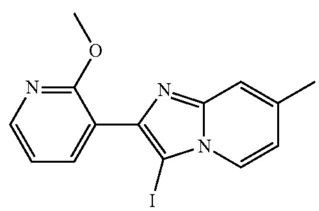 [SMILES: COc1ncccc1-c1nc2cc(C)ccn2c1I] | 3-{3-iodo-7-methylimidazo[1,2-a]pyridin-2-yl}-2-methoxypyridine | 0.87 | 366 | M_2 |

S5) 6-iodo-1-methylisoquinoline

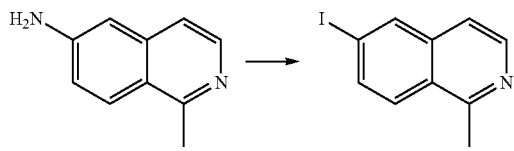

A mixture of 1-methylisoquinolin-6-amine (27 g, 171 mmol) in 2-methylpropan-2-ol (1.5 l) and hydrochloric acid (2 mol/l, 1.5 l) is cooled to 0° C. Sodium nitrite (12 g, 177 mmol) is added and stirring continued for 30 minutes. The mixture is warmed to RT and stirred for 5 minutes before it is cooled to 0° C. again. Sodium iodide (45 g, 302 mmol) is added and the mixture stirred at RT for 30 min. The mixture is diluted with water and extracted with EtOAc. The aqueous phase is made basic with sodium hydroxide and extracted with EtOAc. The combined organic layers are dried over $MgSO_4$ and concentrated in vacuo. The product is purified by RP HPLC. Yield: 5.2 g (11%). HPLC-MS: M+H=270; tR=1.70 mM (METHOD_3).

Assays and Data
XIAP BIR3 and cIAP1 BIR3 Binding Assays (DELFIA)

BIR3 domains of human XIAP (covering amino acids 241 to 356; XIAP BIR3) and cIAP1 (covering amino acids 256 to 363; cIAP1 BIR3) were expressed and purified from *E. coli* as GST-fusion proteins. Peptide AVPIAQKSE-Lys(Biotin), representing the N-terminus of mature human SMAC (SMAC peptide), was used as interaction partner in the protein-peptide interaction assay.

BIR3 domains (10 nM) were incubated with SMAC peptide (10 nM) in assay buffer (50 mM Tris, 120 mM NaCl, 0.1% BSA, 1 mM DTT, 0.05% TritonX100) for one hour at room temperature in the presence of inhibitiory compounds. The assay mixture was transferred to a strepatvidin coated plate and incubated for one hour at room temperature to allow binding of the biotinylated peptide and associated BIR3 domains to the plate. After several washing steps Eu labeled anti-GST antibody (e.g. Perkin Elmer DELFIA Eu-N1-antiGST AD0250) was added to detect BIR3 domain-SMAC peptide interactions according to Perkin Elmer's instructions. Briefly, the antibody was added (dilution 1:5000 in Perkin Elmer DELFIA Assay Buffer 2013-01) and incubated for one hour. After 3 washing steps using Delfia Washing Buffer (Perkin Elmer DELFIA Wash 2013-05), Enhancement Solution (Perkin Elmer Enhancement Asolution 2013-02) was added and incubation continued for 10 minutes. Time resolved Europium fluoresecence was measured in a Wallac Victor using Standard assay settings.

$IC_{50}$ values for inhibitory compounds were calculated from assay results obtained by incubating BIR3 domains with SMAC peptide in the presence of serially diluted compounds (e.g. 1:5). DELFIA assay results were plotted against compound concentrations and Software GraphPad Prizm was used to calculate half maximal inhibitory concentrations ($IC_{50}$ values).

The IC$_{50}$ values representing the biological activity of the examples are listed in the table below. All IC$_{50}$ values are reported in nM and represent the activity of the (S)-isomers:

| # | cIAP1 BIR-3 | XIAP BIR-3 |
|---|---|---|
| (S)-1 | 1 | 207 |
| (S)-2 | 1 | N/A |
| (S)-3 | 1 | 252 |
| (S)-4 | 1 | 303 |
| (S)-5 | 2 | 677 |
| (S)-6 | 1 | 108 |
| (S)-7 | 1 | 124 |
| (S)-8 | 1 | 147 |
| (S)-9 | 1 | 267 |
| (S)-10 | 1 | 260 |
| (S)-11 | 1 | 13 |
| (S)-12 | 2 | 333 |
| (S)-13 | 1 | 219 |
| (S)-14 | 1 | 1269 |
| (S)-15 | 2 | 175 |
| (S)-16 | 2 | 304 |

Cytochrome P450 Isoenzyme Inhibition Assays

The inhibition of the conversion of a specific substrate to its metabolite is assayed at 37° C. with human liver microsomes and used to determine the inhibition of cytochrome P450 isoenzymes. For the following cytochrome P450 isoenzymes these substrates and metabolic reactions are monitored: P450 2C9: hydroxylation of Diclofenac; P450 3A4: hydroxylation of Midazolam; P450 2D6: demethylation of Dextromethorphan; P450 2C19: hydroxylation of Mephenytoin; P450 2C8: deethylation of Amodiaquine.

The final incubation volume contains TRIS buffer (0.1 M), MgCl$_2$ (5 mM), a certain concentration of human liver microsomes dependent on the P450 isoenzyme measured (P450 2C9, P450 3A4: 0.1 mg/ml; P450 2D6: 0.2 mg/ml; P450 2C19: 0.5 mg/ml; P450 2C8: 0.05 mg/ml) and a certain concentration of the individual substrate for each isoenzyme (P450 2C9: Diclofenac 10 µM; P450 3A4: Midazolam 5 µM; P450 2D6: Dextromethorphan 5 µM; P450 2C19: S-Mephenytoin 70 µM; P450 2C8: Amodiaquine 1 µM).

The effect of the test compound is determined at five different concentrations in duplicate (e.g. highest concentration 10-50 µM with subsequent serial 1:4 dilutions) or without test compound (high control). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the IC50 of a positive control inhibitor dependent on the P450 isoenzyme measured (P450 2C9: sulfaphenazole; P450 3A4: ketoconazole; P450 2D6: quinidine; P450 2C19: tranylcypromine; P450 2C8: Montelukast) is determined. The assay results are plotted against compound concentrations to calculated IC$_{50}$ values (half maximal inhibitory concentrations) for inhibitory compounds utilizing Software GraphPad Prizm. The IC$_{50}$ values representing the inhibitory activity of the examples on the individual cytochrome P450 isoenzymes are listed in the table below. All IC$_{50}$ values are reported in µM and represent the inhibitory activity of the (S)-isomers:

| # | P450 2C19 | P450 2C8 | P450 2C9 | P450 2D6 | P450 3A4 |
|---|---|---|---|---|---|
| (S)-1 | >50 | 11 | 38 | 35 | >50 |
| (S)-2 | 1.9 | 0.9 | >50 | >50 | >50 |
| (S)-3 | >50 | 14 | >50 | >50 | >50 |
| (S)-4 | 36 | 9.8 | 27 | 6.4 | >50 |
| (S)-5 | >50 | 1.3 | >50 | >50 | >50 |
| (S)-6 | >50 | 25 | >50 | >50 | >50 |
| (S)-7 | >50 | >50 | >50 | >50 | >50 |
| (S)-8 | 38 | 1.6 | >50 | >50 | >50 |
| (S)-9 | >50 | 15 | >50 | >50 | >50 |
| (S)-10 | >50 | 9.3 | 45 | >50 | >50 |
| (S)-11 | 14 | 15 | >50 | 32 | 46 |
| (S)-12 | >50 | >50 | >50 | >50 | >50 |
| (S)-13 | 12 | 4.5 | >50 | >50 | >50 |
| (S)-14 | >50 | >50 | >50 | >50 | >50 |
| (S)-15 | 32 | 2.2 | 19 | 16 | >50 |
| (S)-16 | >50 | 3.4 | 21 | 29 | >50 |

Solubility Measurement (DMSO Solution Precipitation Method)

A 10 mM DMSO stock solution of a compound is used to determine its aqueous solubility. The DMSO solution is diluted with an aqueous medium (McIlvaine buffer with pH=6.8) to a final concentration of 250 µM. After 24 h of shaking at ambient temperature a potentially formed precipitate is removed by filtration. The concentration of the filtrate is determined by LC-UV methods by comparing the signal to the signal of a reference solution with known concentration.

The solubility of the examples at pH 6.8 is listed in the table below. All values are reported in µg/ml representing the (S)-isomers:

| # | Sol[µg/ml] pH 6.8 |
|---|---|
| (S)-1 | 35 |
| (S)-2 | 8 |
| (S)-3 | 1 |
| (S)-4 | 39 |
| (S)-5 | <1 |
| (S)-6 | 1 |
| (S)-7 | <1 |
| (S)-8 | <1 |
| (S)-9 | 2 |
| (S)-10 | 35 |
| (S)-11 | N/A |
| (S)-12 | <1 |
| (S)-13 | <1 |
| (S)-14 | <1 |
| (S)-15 | 20 |
| (S)-16 | 17 |

On the basis of their biological properties the compounds of general formula (1) according to the invention, their tautomers, racemates, enantiomers, diastereomers, mixtures thereof and the salts of all the above-mentioned forms are suitable for treating diseases characterised by excessive or abnormal cell proliferation.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

Preferred cancers, which may be treated with compounds according to the invention, are lung, liver, colon, brain, breast, ovary, prostate cancer, pancreas, kidney, stomach, head, neck and urothelial cancer, as well as lymphoma and leukemia.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxy-adenosine, 2-fluorodesoxycytidine, 2-methoxyoestradiol, 2C4, 3-alethine, 131-I-TM-601, 3CPA, 7-ethyl-10-hydroxycamptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992, BIBF 1120, bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-IOO, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alfa-2b, interleukin-2, ionafamib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, MLN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, pegfilgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, RAF-265, ramosetron, ranpirnase, RDEA-119/BAY 869766, rebeccamycin analogues, revimid, RG-7167, rhizoxin, rhu-MAb, risedronate, rituximab, rofecoxib, Ro-31-7453, RO-5126766, RPR 109881A, rubidazon, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, xeloda, XELOX, XL-281, XL-518/R-7420, YM-511, YM-598, ZD-4190, ZD-6474, ZD-4054, ZD-0473, ZD-6126, ZD-9331, ZDI839, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:
Examples of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (I) | 80 mg |
| | lactose | 55 mg |
| | corn starch | 190 mg |
| | microcrystalline cellulose | 35 mg |
| | polyvinylpyrrolidone | 15 mg |
| | sodium-carboxymethy starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (I) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula I

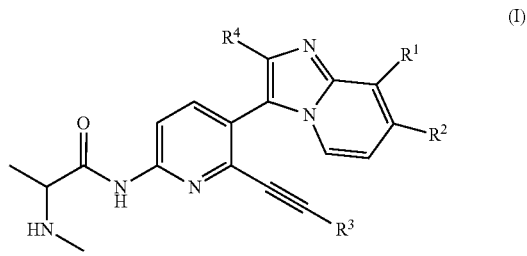

wherein
$R^1$ is selected from the group consisting of hydrogen, —$C_{1-3}$alkyl and halogen;
$R^2$ is selected from the group consisting of hydrogen, —$C_{1-3}$alkyl and halogen;
$R^3$ is selected from the group consisting of phenyl or a 9- to 14-membered heteroaryl wherein each of these groups is optionally substituted with $R^5$ or
$R^3$ is a phenyl moiety fused with a 5-6 membered heterocycloalkyl, wherein each of these groups is optionally and independently substituted with one or more $R^6$;
$R^4$ is a 5- or 6-membered heteroaryl substituted with —$C_{1-3}$alkyl or —O—$C_{1-3}$alkyl;
$R^5$ is —$C_{1-3}$alkyl;
$R^6$ is =O or —$C_{1-3}$ alkyl;
or a pharmaceutically acceptable salt thereof.

2. A compound according to claim 1, wherein $R^1$ is selected from the group consisting of hydrogen, —$CH_3$ and Cl.

3. A compound according to claim 1, wherein $R^2$ is selected from the group consisting of hydrogen, —$CH_3$ and Cl.

4. A compound according to claim 1, wherein $R^1$ is hydrogen and $R^2$ is selected from the group consisting of hydrogen, —$CH_3$ and Cl.

5. A compound according to claim 1, wherein $R^4$ is a 6-membered heteroaryl substituted with —$C_{1-3}$alkyl or —O—$C_{1-3}$alkyl.

6. A compound according to claim 1, wherein $R^4$ is selected from the group consisting of pyridyl, pyrimidinyl, pyrazolyl, imidazolyl, each of which is independently substituted with —$C_{1-3}$alkyl or —O—$C_{1-3}$alkyl.

7. A compound according to claim 1, wherein $R^4$ is selected from the group consisting of pyridyl, pyrimidinyl, pyrazolyl, imidazolyl, each of which is independently substituted with —$CH_3$ or —O—$CH_3$.

8. A pharmaceutical composition comprising a compound according to claim 1 and a pharmaceutically acceptable carrier.

* * * * *